United States Patent
Boudreaux et al.

(10) Patent No.: US 9,757,186 B2
(45) Date of Patent: Sep. 12, 2017

(54) DEVICE STATUS FEEDBACK FOR BIPOLAR TISSUE SPACER

(71) Applicant: Ethicon Endo-Surgery, Inc., Cincinnati, OH (US)

(72) Inventors: Chad P. Boudreaux, Cincinnati, OH (US); David A. Monroe, Milford, OH (US); Rafael J. Ruiz Ortiz, Mason, OH (US); Foster B. Stulen, Mason, OH (US); Jeffrey L. Aldridge, Lebanon, OH (US); Catherine A. Corbett, Cincinnati, OH (US); Terry A. McFarland, Burlington, KY (US)

(73) Assignee: Ethicon LLC, Guaynabo, PR (US)

( * ) Notice: Subject to any disclaimer, the term of this patent is extended or adjusted under 35 U.S.C. 154(b) by 436 days.

(21) Appl. No.: 14/255,242

(22) Filed: Apr. 17, 2014

(65) Prior Publication Data
US 2015/0297286 A1 Oct. 22, 2015

(51) Int. Cl.
*A61B 18/18* (2006.01)
*A61B 18/14* (2006.01)
(Continued)

(52) U.S. Cl.
CPC .. *A61B 18/1445* (2013.01); *A61B 2017/2946* (2013.01); *A61B 2018/0063* (2013.01);
(Continued)

(58) Field of Classification Search
CPC ............ A61B 18/1442; A61B 18/1445; A61B 18/1455
See application file for complete search history.

(56) References Cited

U.S. PATENT DOCUMENTS 2,366,274 A 1/1945 Luth et al.
2,458,152 A 1/1949 Eakins
(Continued)

FOREIGN PATENT DOCUMENTS

CN 2868227 Y 2/2007
DE 4300307 A1 7/1994
(Continued)

OTHER PUBLICATIONS

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
(Continued)

*Primary Examiner* — Ronald Hupczey, Jr.

(57) ABSTRACT

A surgical instrument includes an end effector and a feedback system. The end effector includes a first jaw and a second jaw, wherein at least one of the first jaw and the second jaw is movable relative to the other one of the first jaw and the second jaw to transition the end effector during a closure stroke between an open configuration, a first approximated configuration, and a second approximated configuration. The feedback system includes an indicator, the indicator transitionable between a first indicator position, a second indicator position, and a third indicator position, wherein the indicator is in the first indicator position when the end effect is in the open configuration, wherein the indicator is in the second indicator position when the end effector is in the first approximated configuration, and wherein the indicator is in the third indicator position when the end effector is in the second approximated configuration.

17 Claims, 16 Drawing Sheets

(51) Int. Cl.
 *A61B 18/00* (2006.01)
 *A61B 17/29* (2006.01)
 *A61B 90/00* (2016.01)
(52) U.S. Cl.
 CPC .......... *A61B 2018/00607* (2013.01); *A61B 2018/00958* (2013.01); *A61B 2018/1455* (2013.01); *A61B 2018/1457* (2013.01); *A61B 2090/0801* (2016.02); *A61B 2090/0811* (2016.02)

(56) References Cited

U.S. PATENT DOCUMENTS

| | | |
|---|---|---|
| 2,510,693 A | 6/1950 | Green |
| 2,867,039 A | 1/1959 | Zach |
| 3,166,971 A | 1/1965 | Stoecker |
| 3,525,912 A | 8/1970 | Wallin |
| 3,580,841 A | 5/1971 | Cadotte et al. |
| 3,703,651 A | 11/1972 | Blowers |
| 3,777,760 A | 12/1973 | Essner |
| 4,005,714 A | 2/1977 | Hiltebrandt |
| 4,034,762 A | 7/1977 | Cosens et al. |
| 4,058,126 A | 11/1977 | Leveen |
| 4,203,430 A | 5/1980 | Takahashi |
| 4,220,154 A | 9/1980 | Semm |
| 4,237,441 A | 12/1980 | van Konynenburg et al. |
| 4,281,785 A | 8/1981 | Brooks |
| 4,304,987 A | 12/1981 | van Konynenburg |
| 4,463,759 A | 8/1984 | Garito et al. |
| 4,492,231 A | 1/1985 | Auth |
| 4,535,773 A | 8/1985 | Yoon |
| 4,545,926 A | 10/1985 | Fouts, Jr. et al. |
| 4,550,870 A | 11/1985 | Krumme et al. |
| 4,582,236 A | 4/1986 | Hirose |
| 4,617,927 A | 10/1986 | Manes |
| 4,735,603 A | 4/1988 | Goodson et al. |
| 4,761,871 A | 8/1988 | O'Connor et al. |
| 4,830,462 A | 5/1989 | Karny et al. |
| 4,849,133 A | 7/1989 | Yoshida et al. |
| 4,860,745 A | 8/1989 | Farin et al. |
| 4,878,493 A | 11/1989 | Pasternak et al. |
| 4,880,015 A | 11/1989 | Nierman |
| 4,910,389 A | 3/1990 | Sherman et al. |
| 4,920,978 A | 5/1990 | Colvin |
| 4,936,842 A | 6/1990 | D'Amelio et al. |
| 5,020,514 A | 6/1991 | Heckele |
| 5,061,269 A | 10/1991 | Muller |
| 5,099,840 A | 3/1992 | Goble et al. |
| 5,104,025 A | 4/1992 | Main et al. |
| 5,106,538 A | 4/1992 | Barma et al. |
| 5,108,383 A | 4/1992 | White |
| 5,156,633 A | 10/1992 | Smith |
| 5,160,334 A | 11/1992 | Billings et al. |
| 5,190,541 A | 3/1993 | Abele et al. |
| 5,196,007 A | 3/1993 | Ellman et al. |
| 5,205,459 A | 4/1993 | Brinkerhoff et al. |
| 5,217,460 A | 6/1993 | Knoepfler |
| 5,234,428 A | 8/1993 | Kaufman |
| 5,258,006 A | 11/1993 | Rydell et al. |
| 5,285,945 A | 2/1994 | Brinkerhoff et al. |
| 5,290,286 A | 3/1994 | Parins |
| 5,309,927 A | 5/1994 | Welch |
| 5,312,023 A | 5/1994 | Green et al. |
| 5,318,563 A | 6/1994 | Malis et al. |
| 5,318,564 A | 6/1994 | Eggers |
| 5,318,589 A | 6/1994 | Lichtman |
| 5,326,013 A | 7/1994 | Green et al. |
| 5,330,471 A | 7/1994 | Eggers |
| 5,330,502 A | 7/1994 | Hassler et al. |
| 5,339,723 A | 8/1994 | Huitema |
| 5,342,359 A | 8/1994 | Rydell |
| 5,361,583 A | 11/1994 | Huitema |
| 5,383,874 A | 1/1995 | Jackson et al. |
| 5,387,207 A | 2/1995 | Dyer et al. |
| 5,389,098 A | 2/1995 | Tsuruta et al. |
| 5,395,312 A | 3/1995 | Desai |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,403,312 A | 4/1995 | Yates et al. |
| 5,417,709 A | 5/1995 | Slater |
| 5,428,504 A | 6/1995 | Bhatla |
| 5,429,131 A | 7/1995 | Scheinman et al. |
| 5,443,463 A | 8/1995 | Stern et al. |
| 5,445,638 A | 8/1995 | Rydell et al. |
| 5,451,227 A | 9/1995 | Michaelson |
| 5,456,684 A | 10/1995 | Schmidt et al. |
| 5,458,598 A | 10/1995 | Feinberg et al. |
| 5,465,895 A | 11/1995 | Knodel et al. |
| 5,472,443 A | 12/1995 | Cordis et al. |
| 5,476,479 A | 12/1995 | Green et al. |
| 5,478,003 A | 12/1995 | Green et al. |
| 5,480,409 A | 1/1996 | Riza |
| 5,484,436 A | 1/1996 | Eggers et al. |
| 5,486,189 A | 1/1996 | Mudry et al. |
| 5,496,317 A | 3/1996 | Goble et al. |
| 5,504,650 A | 4/1996 | Katsui et al. |
| 5,509,922 A | 4/1996 | Aranyi et al. |
| 5,511,556 A | 4/1996 | DeSantis |
| 5,520,704 A | 5/1996 | Castro et al. |
| 5,522,839 A | 6/1996 | Pilling |
| 5,531,744 A | 7/1996 | Nardella et al. |
| 5,540,681 A | 7/1996 | Strul et al. |
| 5,542,916 A | 8/1996 | Hirsch et al. |
| 5,558,671 A | 9/1996 | Yates |
| 5,563,179 A | 10/1996 | Stone et al. |
| 5,569,164 A | 10/1996 | Lurz |
| 5,571,121 A | 11/1996 | Heifetz |
| 5,573,534 A | 11/1996 | Stone |
| 5,584,830 A | 12/1996 | Ladd et al. |
| 5,599,350 A | 2/1997 | Schulze et al. |
| 5,607,450 A | 3/1997 | Zvenyatsky et al. |
| 5,611,813 A | 3/1997 | Lichtman |
| 5,618,307 A | 4/1997 | Donlon et al. |
| 5,624,452 A | 4/1997 | Yates |
| 5,632,432 A | 5/1997 | Schulze et al. |
| 5,647,871 A | 7/1997 | Levine et al. |
| 5,658,281 A | 8/1997 | Heard |
| 5,662,667 A | 9/1997 | Knodel |
| 5,665,085 A | 9/1997 | Nardella |
| 5,665,100 A | 9/1997 | Yoon |
| 5,674,219 A | 10/1997 | Monson et al. |
| 5,674,220 A | 10/1997 | Fox et al. |
| 5,688,270 A | 11/1997 | Yates et al. |
| 5,693,051 A | 12/1997 | Schulze et al. |
| 5,709,680 A | 1/1998 | Yates et al. |
| 5,711,472 A | 1/1998 | Bryan |
| 5,713,896 A | 2/1998 | Nardella |
| 5,716,366 A | 2/1998 | Yates |
| 5,720,742 A | 2/1998 | Zacharias |
| 5,720,744 A | 2/1998 | Eggleston et al. |
| 5,735,848 A | 4/1998 | Yates et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,796,188 A | 8/1998 | Bays |
| 5,797,941 A | 8/1998 | Schulze et al. |
| 5,800,432 A | 9/1998 | Swanson |
| 5,800,449 A | 9/1998 | Wales |
| 5,805,140 A | 9/1998 | Rosenberg et al. |
| 5,807,393 A | 9/1998 | Williamson, IV et al. |
| 5,810,811 A | 9/1998 | Yates et al. |
| 5,817,033 A | 10/1998 | DeSantis et al. |
| 5,817,084 A | 10/1998 | Jensen |
| 5,817,093 A | 10/1998 | Williamson, IV et al. |
| 5,827,323 A | 10/1998 | Klieman et al. |
| 5,836,909 A | 11/1998 | Cosmescu |
| 5,836,943 A | 11/1998 | Miller, III |

(56) References Cited

U.S. PATENT DOCUMENTS

| | | |
|---|---|---|
| 5,836,990 A | 11/1998 | Li |
| 5,853,412 A | 12/1998 | Mayenberger |
| 5,876,401 A | 3/1999 | Schulze et al. |
| 5,878,193 A | 3/1999 | Wang et al. |
| 5,880,668 A | 3/1999 | Hall |
| 5,891,142 A | 4/1999 | Eggers et al. |
| 5,906,625 A | 5/1999 | Bito et al. |
| 5,910,129 A | 6/1999 | Koblish et al. |
| 5,921,956 A | 7/1999 | Grinberg et al. |
| 5,929,846 A | 7/1999 | Rosenberg et al. |
| 5,984,938 A | 11/1999 | Yoon |
| 6,003,517 A | 12/1999 | Sheffield et al. |
| 6,013,052 A | 1/2000 | Durman et al. |
| 6,024,741 A * | 2/2000 | Williamson, IV ............ A61B 17/07207 606/40 |
| 6,024,744 A | 2/2000 | Kese et al. |
| 6,033,399 A | 3/2000 | Gines |
| 6,039,734 A | 3/2000 | Goble |
| 6,050,996 A | 4/2000 | Schmaltz et al. |
| 6,063,098 A | 5/2000 | Houser et al. |
| 6,068,629 A | 5/2000 | Haissaguerre et al. |
| 6,074,389 A | 6/2000 | Levine et al. |
| 6,091,995 A | 7/2000 | Ingle et al. |
| 6,099,483 A | 8/2000 | Palmer et al. |
| 6,099,550 A | 8/2000 | Yoon |
| H1904 H | 10/2000 | Yates et al. |
| 6,132,368 A | 10/2000 | Cooper |
| 6,144,402 A | 11/2000 | Norsworthy et al. |
| 6,152,923 A | 11/2000 | Ryan |
| 6,154,198 A | 11/2000 | Rosenberg |
| 6,162,208 A | 12/2000 | Hipps |
| 6,174,309 B1 | 1/2001 | Wrublewski et al. |
| 6,176,857 B1 | 1/2001 | Ashley |
| 6,190,386 B1 | 2/2001 | Rydell |
| 6,206,876 B1 | 3/2001 | Levine et al. |
| 6,228,080 B1 | 5/2001 | Gines |
| 6,231,565 B1 | 5/2001 | Tovey et al. |
| 6,259,230 B1 | 7/2001 | Chou |
| 6,277,117 B1 | 8/2001 | Tetzlaff et al. |
| 6,292,700 B1 | 9/2001 | Morrison et al. |
| 6,325,799 B1 | 12/2001 | Goble |
| 6,340,878 B1 | 1/2002 | Oglesbee |
| 6,364,888 B1 | 4/2002 | Niemeyer et al. |
| 6,387,109 B1 | 5/2002 | Davison et al. |
| 6,391,026 B1 | 5/2002 | Hung et al. |
| 6,398,779 B1 | 6/2002 | Buysse et al. |
| H2037 H | 7/2002 | Yates et al. |
| 6,419,675 B1 | 7/2002 | Gallo, Sr. |
| 6,430,446 B1 | 8/2002 | Knowlton |
| 6,443,968 B1 | 9/2002 | Holthaus et al. |
| 6,458,128 B1 | 10/2002 | Schulze |
| 6,464,689 B1 | 10/2002 | Qin et al. |
| 6,464,702 B2 | 10/2002 | Schulze et al. |
| 6,480,796 B2 | 11/2002 | Wiener |
| 6,491,690 B1 | 12/2002 | Goble et al. |
| 6,500,112 B1 | 12/2002 | Khouri |
| 6,500,176 B1 | 12/2002 | Truckai et al. |
| 6,503,248 B1 | 1/2003 | Levine |
| 6,511,480 B1 | 1/2003 | Tetzlaff et al. |
| 6,514,252 B2 | 2/2003 | Nezhat et al. |
| 6,517,565 B1 | 2/2003 | Whitman et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,551,309 B1 | 4/2003 | LePivert |
| 6,554,829 B2 | 4/2003 | Schulze et al. |
| 6,558,376 B2 | 5/2003 | Bishop |
| 6,562,037 B2 | 5/2003 | Paton et al. |
| 6,572,639 B1 | 6/2003 | Ingle et al. |
| 6,575,969 B1 | 6/2003 | Rittman, III et al. |
| 6,582,451 B1 | 6/2003 | Marucci et al. |
| 6,584,360 B2 | 6/2003 | Francischelli et al. |
| 6,585,735 B1 | 7/2003 | Lands et al. |
| 6,589,200 B1 | 7/2003 | Schwemberger et al. |
| 6,602,252 B2 | 8/2003 | Mollenauer |
| 6,619,529 B2 | 9/2003 | Green et al. |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,635,057 B2 | 10/2003 | Harano et al. |
| 6,644,532 B2 | 11/2003 | Green et al. |
| 6,651,669 B1 | 11/2003 | Burnside |
| 6,656,177 B2 | 12/2003 | Truckai et al. |
| 6,656,198 B2 | 12/2003 | Tsonton et al. |
| 6,662,127 B2 | 12/2003 | Wiener et al. |
| 6,673,248 B2 | 1/2004 | Chowdhury |
| 6,679,882 B1 | 1/2004 | Kornerup |
| 6,695,840 B2 | 2/2004 | Schulze |
| 6,722,552 B2 | 4/2004 | Fenton, Jr. |
| 6,733,498 B2 | 5/2004 | Paton et al. |
| 6,746,443 B1 | 6/2004 | Morley et al. |
| 6,752,815 B2 | 6/2004 | Beaupre |
| 6,770,072 B1 | 8/2004 | Truckai et al. |
| 6,773,409 B2 | 8/2004 | Truckai et al. |
| 6,773,435 B2 | 8/2004 | Schulze et al. |
| 6,775,575 B2 | 8/2004 | Bommannan et al. |
| 6,783,524 B2 | 8/2004 | Anderson et al. |
| 6,789,939 B2 | 9/2004 | Schrödinger et al. |
| 6,796,981 B2 | 9/2004 | Wham et al. |
| 6,800,085 B2 | 10/2004 | Selmon et al. |
| 6,802,843 B2 | 10/2004 | Truckai et al. |
| 6,811,842 B1 | 11/2004 | Ehrnsperger et al. |
| 6,821,273 B2 | 11/2004 | Mollenauer |
| 6,835,199 B2 | 12/2004 | McGuckin, Jr. et al. |
| 6,840,938 B1 | 1/2005 | Morley et al. |
| 6,860,880 B2 | 3/2005 | Treat et al. |
| 6,877,647 B2 | 4/2005 | Ratcliff et al. |
| 6,893,435 B2 | 5/2005 | Goble |
| 6,905,497 B2 | 6/2005 | Truckai et al. |
| 6,908,463 B2 | 6/2005 | Treat et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,644 B2 | 8/2005 | Truckai et al. |
| 6,953,461 B2 | 10/2005 | McClurken et al. |
| 6,977,495 B2 | 12/2005 | Donofrio |
| 6,994,709 B2 | 2/2006 | Iida |
| 7,000,818 B2 | 2/2006 | Shelton, IV et al. |
| 7,011,657 B2 | 3/2006 | Truckai et al. |
| 7,041,102 B2 | 5/2006 | Truckai et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,936 B2 | 6/2006 | Ryan |
| 7,070,597 B2 | 7/2006 | Truckai et al. |
| 7,077,853 B2 | 7/2006 | Kramer et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,094,235 B2 | 8/2006 | Francischelli |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,112,201 B2 | 9/2006 | Truckai et al. |
| 7,118,570 B2 | 10/2006 | Tetzlaff et al. |
| 7,125,409 B2 | 10/2006 | Truckai et al. |
| 7,131,970 B2 | 11/2006 | Moses et al. |
| 7,137,980 B2 | 11/2006 | Buysse et al. |
| 7,143,925 B2 | 12/2006 | Shelton, IV et al. |
| 7,147,138 B2 | 12/2006 | Shelton, IV |
| 7,156,846 B2 | 1/2007 | Dycus et al. |
| 7,160,296 B2 | 1/2007 | Pearson et al. |
| 7,169,146 B2 | 1/2007 | Truckai et al. |
| 7,169,156 B2 | 1/2007 | Hart |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,195,631 B2 | 3/2007 | Dumbauld |
| 7,207,471 B2 | 4/2007 | Heinrich et al. |
| 7,220,951 B2 | 5/2007 | Truckai et al. |
| 7,225,964 B2 | 6/2007 | Mastri et al. |
| 7,226,448 B2 | 6/2007 | Bertolero et al. |

(56) References Cited

U.S. PATENT DOCUMENTS

| | | |
|---|---|---|
| 7,232,440 B2 | 6/2007 | Dumbauld et al. |
| 7,235,073 B2 | 6/2007 | Levine et al. |
| 7,241,294 B2 | 7/2007 | Reschke |
| 7,251,531 B2 | 7/2007 | Mosher et al. |
| 7,252,667 B2 | 8/2007 | Moses et al. |
| 7,267,677 B2 | 9/2007 | Johnson et al. |
| 7,267,685 B2 | 9/2007 | Butaric et al. |
| 7,273,483 B2 | 9/2007 | Wiener et al. |
| 7,287,682 B1 | 10/2007 | Ezzat et al. |
| 7,300,450 B2 | 11/2007 | Vleugels et al. |
| 7,303,557 B2 | 12/2007 | Wham et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,329,257 B2 | 2/2008 | Kanehira et al. |
| 7,354,440 B2 | 4/2008 | Truckal et al. |
| 7,357,287 B2 | 4/2008 | Shelton, IV et al. |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,381,209 B2 | 6/2008 | Truckai et al. |
| 7,384,420 B2 | 6/2008 | Dycus et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,416,101 B2 | 8/2008 | Shelton, IV et al. |
| 7,422,139 B2 | 9/2008 | Shelton, IV et al. |
| 7,435,582 B2 | 10/2008 | Zimmermann et al. |
| 7,441,684 B2 | 10/2008 | Shelton, IV et al. |
| 7,442,193 B2 | 10/2008 | Shields et al. |
| 7,445,621 B2 | 11/2008 | Dumbauld et al. |
| 7,464,846 B2 | 12/2008 | Shelton, IV et al. |
| 7,473,253 B2 | 1/2009 | Dycus et al. |
| 7,488,319 B2 | 2/2009 | Yates |
| 7,491,201 B2 | 2/2009 | Shields et al. |
| 7,494,501 B2 | 2/2009 | Ahlberg et al. |
| 7,498,080 B2 | 3/2009 | Tung et al. |
| 7,506,791 B2 | 3/2009 | Omaits et al. |
| 7,510,107 B2 | 3/2009 | Timm et al. |
| 7,513,025 B2 | 4/2009 | Fischer |
| 7,517,349 B2 | 4/2009 | Truckai et al. |
| 7,524,320 B2 | 4/2009 | Tierney et al. |
| 7,540,872 B2 | 6/2009 | Schechter et al. |
| 7,543,730 B1 | 6/2009 | Marczyk |
| 7,550,216 B2 | 6/2009 | Ofer et al. |
| 7,553,309 B2 | 6/2009 | Buysse et al. |
| 7,559,452 B2 | 7/2009 | Wales et al. |
| 7,582,086 B2 | 9/2009 | Privitera et al. |
| 7,586,289 B2 | 9/2009 | Andruk et al. |
| 7,588,176 B2 | 9/2009 | Timm et al. |
| 7,594,925 B2 | 9/2009 | Danek et al. |
| 7,597,693 B2 | 10/2009 | Garrison |
| 7,604,150 B2 | 10/2009 | Boudreaux |
| 7,621,930 B2 | 11/2009 | Houser |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,277 B2 | 1/2010 | McClurken et al. |
| 7,648,499 B2 | 1/2010 | Orszulak et al. |
| 7,658,311 B2 | 2/2010 | Boudreaux |
| 7,665,647 B2 | 2/2010 | Shelton, IV et al. |
| 7,666,206 B2 | 2/2010 | Taniguchi et al. |
| 7,670,334 B2 | 3/2010 | Hueil et al. |
| 7,691,095 B2 | 4/2010 | Bednarek et al. |
| 7,691,098 B2 | 4/2010 | Wallace et al. |
| 7,703,459 B2 | 4/2010 | Saadat et al. |
| 7,703,653 B2 | 4/2010 | Shah et al. |
| 7,708,751 B2 | 5/2010 | Hughes et al. |
| 7,717,915 B2 | 5/2010 | Miyazawa |
| 7,722,527 B2 | 5/2010 | Bouchier et al. |
| 7,722,607 B2 | 5/2010 | Dumbauld et al. |
| 7,726,537 B2 | 6/2010 | Olson et al. |
| 7,753,904 B2 | 7/2010 | Shelton, IV et al. |
| 7,753,908 B2 | 7/2010 | Swanson |
| 7,762,445 B2 | 7/2010 | Heinrich et al. |
| 7,766,210 B2 | 8/2010 | Shelton, IV et al. |
| 7,766,910 B2 | 8/2010 | Hixson et al. |
| 7,770,775 B2 | 8/2010 | Shelton, IV et al. |
| 7,775,972 B2 | 8/2010 | Brock et al. |
| 7,776,037 B2 | 8/2010 | Odom |
| 7,780,651 B2 | 8/2010 | Madhani et al. |
| 7,780,663 B2 | 8/2010 | Yates et al. |
| 7,784,663 B2 | 8/2010 | Shelton, IV |
| 7,789,883 B2 | 9/2010 | Takashino et al. |
| 7,793,814 B2 | 9/2010 | Racenet et al. |
| 7,803,156 B2 | 9/2010 | Eder et al. |
| 7,806,891 B2 | 10/2010 | Nowlin et al. |
| 7,810,693 B2 | 10/2010 | Broehl et al. |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,872 B2 | 10/2010 | Johnson et al. |
| 7,824,401 B2 | 11/2010 | Manzo et al. |
| 7,832,408 B2 | 11/2010 | Shelton, IV et al. |
| 7,832,612 B2 | 11/2010 | Baxter, III et al. |
| 7,845,537 B2 | 12/2010 | Shelton, IV et al. |
| 7,846,159 B2 | 12/2010 | Morrison et al. |
| 7,846,160 B2 | 12/2010 | Payne et al. |
| 7,861,906 B2 | 1/2011 | Doll et al. |
| 7,879,035 B2 | 2/2011 | Garrison et al. |
| 7,879,070 B2 | 2/2011 | Ortiz et al. |
| 7,896,875 B2 | 3/2011 | Heim et al. |
| 7,901,400 B2 | 3/2011 | Wham et al. |
| 7,909,220 B2 | 3/2011 | Viola |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,931,649 B2 | 4/2011 | Couture et al. |
| 7,935,114 B2 | 5/2011 | Takashino et al. |
| 7,951,165 B2 | 5/2011 | Golden et al. |
| 7,955,331 B2 | 6/2011 | Truckai et al. |
| 7,963,963 B2 | 6/2011 | Francischelli et al. |
| 7,967,602 B2 | 6/2011 | Lindquist |
| 7,981,113 B2 | 7/2011 | Truckai et al. |
| 7,997,278 B2 | 8/2011 | Utley et al. |
| 8,020,743 B2 | 9/2011 | Shelton, IV |
| 8,038,693 B2 | 10/2011 | Allen |
| 8,056,720 B2 | 11/2011 | Hawkes |
| 8,058,771 B2 | 11/2011 | Giordano et al. |
| 8,061,014 B2 | 11/2011 | Smith et al. |
| 8,070,036 B1 | 12/2011 | Knodel |
| 8,105,323 B2 | 1/2012 | Buysse et al. |
| 8,128,624 B2 | 3/2012 | Couture et al. |
| 8,136,712 B2 | 3/2012 | Zingman |
| 8,141,762 B2 | 3/2012 | Bedi et al. |
| 8,157,145 B2 | 4/2012 | Shelton, IV et al. |
| 8,197,472 B2 | 6/2012 | Lau et al. |
| 8,197,479 B2 | 6/2012 | Olson et al. |
| 8,197,502 B2 | 6/2012 | Smith et al. |
| 8,221,415 B2 | 7/2012 | Francischelli |
| 8,236,020 B2 | 8/2012 | Smith et al. |
| 8,241,235 B2 | 8/2012 | Kahler et al. |
| 8,241,284 B2 | 8/2012 | Dycus et al. |
| 8,246,615 B2 | 8/2012 | Behnke |
| 8,246,618 B2 | 8/2012 | Bucciaglia et al. |
| 8,251,994 B2 | 8/2012 | McKenna et al. |
| 8,262,563 B2 | 9/2012 | Bakos et al. |
| 8,267,300 B2 | 9/2012 | Boudreaux |
| 8,277,446 B2 | 10/2012 | Heard |
| 8,277,447 B2 | 10/2012 | Garrison et al. |
| 8,282,669 B2 | 10/2012 | Gerber et al. |
| 8,287,528 B2 | 10/2012 | Wham et al. |
| 8,292,886 B2 | 10/2012 | Kerr et al. |
| 8,298,232 B2 | 10/2012 | Unger |
| 8,303,583 B2 | 11/2012 | Hosier et al. |
| 8,323,310 B2 | 12/2012 | Kingsley |
| 8,333,778 B2 | 12/2012 | Smith et al. |
| 8,333,779 B2 | 12/2012 | Smith et al. |

(56) References Cited

U.S. PATENT DOCUMENTS

| | | |
|---|---|---|
| 8,334,468 B2 | 12/2012 | Palmer et al. |
| 8,338,726 B2 | 12/2012 | Palmer et al. |
| 8,357,158 B2 | 1/2013 | McKenna et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,377,059 B2 | 2/2013 | Deville et al. |
| 8,377,085 B2 | 2/2013 | Smith et al. |
| 8,397,971 B2 | 3/2013 | Yates et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,414,577 B2 | 4/2013 | Boudreaux et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,425,545 B2 | 4/2013 | Smith et al. |
| 8,430,876 B2 * | 4/2013 | Kappus .............. A61B 18/1445 606/51 |
| 8,435,257 B2 | 5/2013 | Smith et al. |
| 8,439,939 B2 | 5/2013 | Deville et al. |
| 8,444,662 B2 | 5/2013 | Palmer et al. |
| 8,444,664 B2 | 5/2013 | Balanev et al. |
| 8,453,906 B2 | 6/2013 | Huang et al. |
| 8,460,288 B2 | 6/2013 | Tamai et al. |
| 8,460,292 B2 | 6/2013 | Truckai et al. |
| 8,480,703 B2 | 7/2013 | Nicholas et al. |
| 8,485,413 B2 | 7/2013 | Scheib et al. |
| 8,486,057 B2 | 7/2013 | Behnke, II |
| 8,496,682 B2 | 7/2013 | Guerra et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,562,598 B2 | 10/2013 | Falkenstein et al. |
| 8,562,604 B2 | 10/2013 | Nishimura |
| 8,568,390 B2 | 10/2013 | Mueller |
| 8,568,412 B2 | 10/2013 | Brandt et al. |
| 8,569,997 B2 | 10/2013 | Lee |
| 8,574,231 B2 | 11/2013 | Boudreaux et al. |
| 8,591,506 B2 | 11/2013 | Wham et al. |
| D695,407 S | 12/2013 | Price et al. |
| 8,613,383 B2 | 12/2013 | Beckman et al. |
| 8,623,011 B2 | 1/2014 | Spivey |
| 8,623,016 B2 | 1/2014 | Fischer |
| 8,623,027 B2 | 1/2014 | Price et al. |
| 8,623,044 B2 | 1/2014 | Timm et al. |
| 8,628,529 B2 | 1/2014 | Aldridge et al. |
| 8,632,461 B2 | 1/2014 | Glossop |
| 8,638,428 B2 | 1/2014 | Brown |
| 8,647,350 B2 | 2/2014 | Mohan et al. |
| 8,663,220 B2 | 3/2014 | Wiener et al. |
| 8,663,222 B2 | 3/2014 | Anderson et al. |
| 8,684,253 B2 | 4/2014 | Giordano et al. |
| 8,685,020 B2 | 4/2014 | Weizman et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,709,035 B2 | 4/2014 | Johnson et al. |
| 8,715,270 B2 | 5/2014 | Weitzner et al. |
| 8,715,277 B2 | 5/2014 | Weizman |
| 8,734,443 B2 | 5/2014 | Hixson et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,764,747 B2 | 7/2014 | Cummings et al. |
| 8,790,342 B2 | 7/2014 | Stulen et al. |
| 8,795,276 B2 | 8/2014 | Dietz et al. |
| 8,795,327 B2 | 8/2014 | Dietz et al. |
| 8,827,992 B2 | 9/2014 | Koss et al. |
| 8,834,466 B2 | 9/2014 | Cummings et al. |
| 8,834,518 B2 | 9/2014 | Faller et al. |
| 8,845,630 B2 | 9/2014 | Mehta et al. |
| 8,888,776 B2 | 11/2014 | Dietz et al. |
| 8,888,809 B2 | 11/2014 | Davison et al. |
| 8,906,016 B2 | 12/2014 | Boudreaux et al. |
| 8,926,607 B2 | 1/2015 | Norvell et al. |
| 8,926,608 B2 | 1/2015 | Bacher et al. |
| 8,931,682 B2 | 1/2015 | Timm et al. |
| 8,939,974 B2 | 1/2015 | Boudreaux et al. |
| 8,951,248 B2 | 2/2015 | Messerly et al. |
| 8,956,349 B2 | 2/2015 | Aldridge et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,302 B2 | 3/2015 | Aldridge et al. |
| 8,992,422 B2 | 3/2015 | Spivey et al. |
| 9,005,199 B2 | 4/2015 | Beckman et al. |
| 9,011,437 B2 | 4/2015 | Woodruff et al. |
| 9,028,494 B2 | 5/2015 | Shelton, IV et al. |
| 9,028,519 B2 | 5/2015 | Yates et al. |
| 9,044,243 B2 | 6/2015 | Johnson et al. |
| 9,044,256 B2 | 6/2015 | Cadeddu et al. |
| 9,055,961 B2 | 6/2015 | Manzo et al. |
| 9,060,770 B2 | 6/2015 | Shelton, IV et al. |
| 9,066,723 B2 | 6/2015 | Beller et al. |
| 9,072,535 B2 | 7/2015 | Shelton, IV et al. |
| 9,072,536 B2 | 7/2015 | Shelton, IV et al. |
| 9,101,385 B2 | 8/2015 | Shelton, IV et al. |
| 9,119,657 B2 | 9/2015 | Shelton, IV et al. |
| 9,125,662 B2 | 9/2015 | Shelton, IV |
| 9,149,324 B2 | 10/2015 | Huang et al. |
| 9,149,325 B2 | 10/2015 | Worrell et al. |
| 9,168,085 B2 | 10/2015 | Juzkiw et al. |
| 9,179,912 B2 | 11/2015 | Yates et al. |
| 9,192,380 B2 | 11/2015 | (Tarinelli) Racenet et al. |
| 9,192,431 B2 | 11/2015 | Woodruff et al. |
| 9,198,714 B2 | 12/2015 | Worrell et al. |
| 9,204,879 B2 | 12/2015 | Shelton, IV |
| 9,216,050 B2 | 12/2015 | Condie et al. |
| 9,226,751 B2 | 1/2016 | Shelton, IV et al. |
| 9,226,767 B2 | 1/2016 | Stulen et al. |
| 9,237,891 B2 | 1/2016 | Shelton, IV |
| 9,259,265 B2 | 2/2016 | Harris et al. |
| 9,265,926 B2 | 2/2016 | Strobl et al. |
| 9,277,962 B2 | 3/2016 | Koss et al. |
| 9,283,027 B2 | 3/2016 | Monson et al. |
| 9,283,045 B2 | 3/2016 | Rhee et al. |
| 9,295,514 B2 | 3/2016 | Shelton, IV et al. |
| 9,314,292 B2 | 4/2016 | Trees et al. |
| 9,326,788 B2 | 5/2016 | Batross et al. |
| 9,333,025 B2 | 5/2016 | Monson et al. |
| 9,351,754 B2 | 5/2016 | Vakharia et al. |
| 9,375,232 B2 | 6/2016 | Hunt et al. |
| 9,375,267 B2 | 6/2016 | Kerr et al. |
| 9,408,660 B2 | 8/2016 | Strobl et al. |
| 9,414,880 B2 | 8/2016 | Monson et al. |
| 9,421,060 B2 | 8/2016 | Monson et al. |
| 9,456,863 B2 | 10/2016 | Moua |
| 9,456,864 B2 | 10/2016 | Witt et al. |
| 9,510,906 B2 | 12/2016 | Boudreaux et al. |
| 2002/0022836 A1 | 2/2002 | Goble et al. |
| 2002/0049551 A1 | 4/2002 | Friedman et al. |
| 2002/0107517 A1 | 8/2002 | Witt et al. |
| 2002/0165541 A1 | 11/2002 | Whitman |
| 2003/0014053 A1 | 1/2003 | Nguyen et al. |
| 2003/0105474 A1 | 6/2003 | Bonutti |
| 2003/0109875 A1 | 6/2003 | Tetzlaff et al. |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0158548 A1 | 8/2003 | Phan et al. |
| 2003/0171747 A1 | 9/2003 | Kanehira et al. |
| 2003/0216722 A1 | 11/2003 | Swanson |
| 2003/0229344 A1 | 12/2003 | Dycus et al. |
| 2004/0019350 A1 | 1/2004 | O'Brien et al. |
| 2004/0054364 A1 | 3/2004 | Aranyi et al. |
| 2004/0092992 A1 | 5/2004 | Adams et al. |
| 2004/0138621 A1 | 7/2004 | Jahns et al. |
| 2004/0167508 A1 | 8/2004 | Wham et al. |
| 2004/0193148 A1 | 9/2004 | Wham et al. |

(56) References Cited

U.S. PATENT DOCUMENTS

| | | |
|---|---|---|
| 2004/0193150 A1 | 9/2004 | Sharkey et al. |
| 2004/0232196 A1 | 11/2004 | Shelton, IV et al. |
| 2004/0249374 A1 | 12/2004 | Tetzlaff et al. |
| 2004/0260273 A1 | 12/2004 | Wan |
| 2005/0015125 A1 | 1/2005 | Mioduski et al. |
| 2005/0033278 A1 | 2/2005 | McClurken et al. |
| 2005/0085809 A1 | 4/2005 | Mucko et al. |
| 2005/0090817 A1 | 4/2005 | Phan |
| 2005/0103819 A1 | 5/2005 | Racenet et al. |
| 2005/0131390 A1 | 6/2005 | Heinrich et al. |
| 2005/0165429 A1 | 7/2005 | Douglas et al. |
| 2005/0171522 A1 | 8/2005 | Christopherson |
| 2005/0203507 A1 | 9/2005 | Truckai et al. |
| 2005/0256405 A1 | 11/2005 | Makin et al. |
| 2005/0261581 A1 | 11/2005 | Hughes et al. |
| 2005/0267464 A1 | 12/2005 | Truckai et al. |
| 2006/0052778 A1 | 3/2006 | Chapman et al. |
| 2006/0058825 A1 | 3/2006 | Ogura et al. |
| 2006/0064086 A1 | 3/2006 | Odom |
| 2006/0069388 A1 | 3/2006 | Truckai et al. |
| 2006/0159731 A1 | 7/2006 | Shoshan |
| 2006/0270916 A1 | 11/2006 | Skwarek et al. |
| 2006/0293656 A1 | 12/2006 | Shadduck et al. |
| 2007/0027469 A1 | 2/2007 | Smith et al. |
| 2007/0073185 A1 | 3/2007 | Nakao |
| 2007/0073341 A1 | 3/2007 | Smith et al. |
| 2007/0106158 A1 | 5/2007 | Madan et al. |
| 2007/0106317 A1 | 5/2007 | Shelton, IV et al. |
| 2007/0118115 A1 | 5/2007 | Artale et al. |
| 2007/0146113 A1 | 6/2007 | Truckai et al. |
| 2007/0173803 A1 | 7/2007 | Wham et al. |
| 2007/0173811 A1 | 7/2007 | Couture et al. |
| 2007/0173813 A1 | 7/2007 | Odom |
| 2007/0175949 A1 | 8/2007 | Shelton, IV et al. |
| 2007/0185474 A1 | 8/2007 | Nahen |
| 2007/0191713 A1 | 8/2007 | Eichmann et al. |
| 2007/0191830 A1 | 8/2007 | Cromton, Jr. et al. |
| 2007/0203483 A1 | 8/2007 | Kim et al. |
| 2007/0208312 A1 | 9/2007 | Norton et al. |
| 2007/0208340 A1 | 9/2007 | Ganz et al. |
| 2007/0232920 A1 | 10/2007 | Kowalski et al. |
| 2007/0232926 A1 | 10/2007 | Stulen et al. |
| 2007/0232927 A1 | 10/2007 | Madan et al. |
| 2007/0232928 A1 | 10/2007 | Wiener et al. |
| 2007/0236213 A1 | 10/2007 | Paden et al. |
| 2007/0239025 A1 | 10/2007 | Wiener et al. |
| 2007/0260242 A1 | 11/2007 | Dycus et al. |
| 2007/0265613 A1 | 11/2007 | Edelstein et al. |
| 2007/0265616 A1 | 11/2007 | Couture et al. |
| 2008/0015575 A1 | 1/2008 | Odom et al. |
| 2008/0071269 A1 | 3/2008 | Hilario et al. |
| 2008/0114355 A1 | 5/2008 | Whayne et al. |
| 2008/0147058 A1 | 6/2008 | Horrell et al. |
| 2008/0147062 A1 | 6/2008 | Truckai et al. |
| 2008/0167522 A1 | 7/2008 | Giordano et al. |
| 2008/0188755 A1 | 8/2008 | Hart |
| 2008/0188851 A1 | 8/2008 | Truckai et al. |
| 2008/0188912 A1 | 8/2008 | Stone et al. |
| 2008/0214967 A1 | 9/2008 | Aranyi et al. |
| 2008/0221565 A1 | 9/2008 | Eder et al. |
| 2008/0255642 A1 | 10/2008 | Zarins et al. |
| 2008/0262491 A1 | 10/2008 | Swoyer et al. |
| 2008/0269862 A1 | 10/2008 | Elmouelhi et al. |
| 2008/0281315 A1 | 11/2008 | Gines |
| 2008/0294158 A1 | 11/2008 | Pappone et al. |
| 2008/0300588 A1 | 12/2008 | Groth et al. |
| 2009/0012516 A1 | 1/2009 | Curtis et al. |
| 2009/0048589 A1 | 2/2009 | Takashino et al. |
| 2009/0076506 A1 | 3/2009 | Baker |
| 2009/0076534 A1 | 3/2009 | Shelton, IV et al. |
| 2009/0082766 A1 | 3/2009 | Unger et al. |
| 2009/0099582 A1 | 4/2009 | Isaacs et al. |
| 2009/0112229 A1 | 4/2009 | Omori et al. |
| 2009/0125026 A1 | 5/2009 | Rioux et al. |
| 2009/0125027 A1 | 5/2009 | Fischer |
| 2009/0131929 A1 | 5/2009 | Shimizu |
| 2009/0138003 A1 | 5/2009 | Deville et al. |
| 2009/0138006 A1 | 5/2009 | Bales et al. |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0206140 A1 | 8/2009 | Scheib et al. |
| 2009/0209979 A1 | 8/2009 | Yates et al. |
| 2009/0248002 A1 | 10/2009 | Takashino et al. |
| 2009/0248021 A1 | 10/2009 | McKenna |
| 2009/0254080 A1 | 10/2009 | Honda |
| 2009/0287205 A1 | 11/2009 | Ingle |
| 2009/0320268 A1 | 12/2009 | Cunningham et al. |
| 2009/0326530 A1 | 12/2009 | Orban, III et al. |
| 2010/0032470 A1 | 2/2010 | Hess et al. |
| 2010/0036370 A1 | 2/2010 | Mirel et al. |
| 2010/0036380 A1 | 2/2010 | Taylor et al. |
| 2010/0076433 A1 | 3/2010 | Taylor et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0094323 A1 | 4/2010 | Isaacs et al. |
| 2010/0168620 A1 | 7/2010 | Klimovitch et al. |
| 2010/0222752 A1 | 9/2010 | Collins, Jr. et al. |
| 2010/0237132 A1 | 9/2010 | Measamer et al. |
| 2010/0264194 A1 | 10/2010 | Huang et al. |
| 2010/0274278 A1 | 10/2010 | Fleenor et al. |
| 2011/0015627 A1 | 1/2011 | DiNardo et al. |
| 2011/0082486 A1 | 4/2011 | Messerly et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087220 A1 | 4/2011 | Felder et al. |
| 2011/0118754 A1 | 5/2011 | Dachs, II et al. |
| 2011/0155781 A1 | 6/2011 | Swensgard et al. |
| 2011/0224668 A1 | 9/2011 | Johnson et al. |
| 2011/0276049 A1 | 11/2011 | Gerhardt |
| 2011/0276057 A1 | 11/2011 | Conlon et al. |
| 2011/0278343 A1 | 11/2011 | Knodel et al. |
| 2011/0284014 A1 | 11/2011 | Cadeddu et al. |
| 2011/0290856 A1 | 12/2011 | Shelton, IV et al. |
| 2011/0295269 A1 | 12/2011 | Swensgard et al. |
| 2011/0295295 A1 | 12/2011 | Shelton, IV et al. |
| 2011/0301605 A1 | 12/2011 | Horner |
| 2011/0306967 A1 | 12/2011 | Payne et al. |
| 2011/0313415 A1 | 12/2011 | Fernandez et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0078139 A1 | 3/2012 | Aldridge et al. |
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0078248 A1 | 3/2012 | Worrell et al. |
| 2012/0083783 A1 | 4/2012 | Davison et al. |
| 2012/0109186 A1 | 5/2012 | Parrott et al. |
| 2012/0116265 A1 | 5/2012 | Houser et al. |
| 2012/0116379 A1 | 5/2012 | Yates et al. |
| 2012/0116380 A1 | 5/2012 | Madan et al. |
| 2012/0116391 A1 | 5/2012 | Houser et al. |
| 2012/0130256 A1 | 5/2012 | Buysse et al. |
| 2012/0136353 A1 | 5/2012 | Romero |
| 2012/0138660 A1 | 6/2012 | Shelton, IV |
| 2012/0150170 A1 | 6/2012 | Buysse et al. |
| 2012/0150192 A1 | 6/2012 | Dachs, II et al. |
| 2012/0172859 A1 | 7/2012 | Condie et al. |
| 2012/0265196 A1 | 10/2012 | Turner et al. |
| 2012/0265241 A1 | 10/2012 | Hart et al. |
| 2012/0296371 A1 | 11/2012 | Kappus et al. |
| 2012/0323238 A1 | 12/2012 | Tyrrell et al. |
| 2013/0023925 A1 | 1/2013 | Mueller |
| 2013/0030428 A1 | 1/2013 | Worrell et al. |
| 2013/0030433 A1 | 1/2013 | Heard |
| 2013/0035685 A1 | 2/2013 | Fischer et al. |

(56) References Cited

U.S. PATENT DOCUMENTS

| | | |
|---|---|---|
| 2013/0079762 A1 | 3/2013 | Twomey et al. |
| 2013/0085496 A1 | 4/2013 | Unger et al. |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0253256 A1 | 9/2013 | Griffith et al. |
| 2013/0253502 A1 | 9/2013 | Aronow et al. |
| 2013/0296843 A1 | 11/2013 | Boudreaux et al. |
| 2013/0338661 A1 | 12/2013 | Behnke, II |
| 2014/0001231 A1 | 1/2014 | Shelton, IV et al. |
| 2014/0001234 A1 | 1/2014 | Shelton, IV et al. |
| 2014/0001235 A1 | 1/2014 | Shelton, IV |
| 2014/0001236 A1 | 1/2014 | Shelton, IV et al. |
| 2014/0005640 A1 | 1/2014 | Shelton, IV et al. |
| 2014/0005653 A1 | 1/2014 | Shelton, IV et al. |
| 2014/0005678 A1 | 1/2014 | Shelton, IV et al. |
| 2014/0005680 A1 | 1/2014 | Shelton, IV et al. |
| 2014/0005681 A1 | 1/2014 | Gee et al. |
| 2014/0005693 A1 | 1/2014 | Shelton, IV et al. |
| 2014/0005694 A1 | 1/2014 | Shelton, IV et al. |
| 2014/0005695 A1 | 1/2014 | Shelton, IV |
| 2014/0005701 A1 | 1/2014 | Olson et al. |
| 2014/0005702 A1 | 1/2014 | Timm et al. |
| 2014/0005703 A1 | 1/2014 | Stulen et al. |
| 2014/0005705 A1 | 1/2014 | Weir et al. |
| 2014/0005718 A1 | 1/2014 | Shelton, IV et al. |
| 2014/0014544 A1 | 1/2014 | Bugnard et al. |
| 2014/0094801 A1 | 4/2014 | Boudreaux et al. |
| 2014/0180281 A1 | 6/2014 | Rusin |
| 2014/0194874 A1 | 7/2014 | Dietz et al. |
| 2014/0194875 A1 | 7/2014 | Reschke et al. |
| 2014/0194915 A1 | 7/2014 | Johnson et al. |
| 2014/0214019 A1 | 7/2014 | Baxter, III et al. |
| 2014/0228844 A1 | 8/2014 | Hörlle et al. |
| 2014/0257284 A1 | 9/2014 | Artale |
| 2014/0303551 A1 | 10/2014 | Germain et al. |
| 2014/0316408 A1 | 10/2014 | Davison et al. |
| 2014/0330271 A1 | 11/2014 | Dietz et al. |
| 2014/0343550 A1 | 11/2014 | Faller et al. |
| 2015/0018826 A1 | 1/2015 | Boudreaux |
| 2015/0080876 A1 | 3/2015 | Worrell et al. |
| 2015/0080879 A1 | 3/2015 | Trees et al. |
| 2015/0080891 A1 | 3/2015 | Shelton, IV et al. |
| 2015/0133915 A1 | 5/2015 | Strobl et al. |
| 2015/0133929 A1 | 5/2015 | Evans et al. |
| 2015/0141981 A1 | 5/2015 | Price et al. |
| 2015/0190189 A1 | 7/2015 | Yates et al. |
| 2015/0196352 A1 | 7/2015 | Beckman et al. |
| 2015/0230853 A1 | 8/2015 | Johnson et al. |
| 2015/0230861 A1 | 8/2015 | Woloszko et al. |
| 2015/0265347 A1 | 9/2015 | Yates et al. |
| 2015/0272602 A1 | 10/2015 | Boudreaux et al. |
| 2015/0272657 A1 | 10/2015 | Yates et al. |
| 2015/0272659 A1 | 10/2015 | Boudreaux et al. |
| 2015/0272660 A1 | 10/2015 | Boudreaux et al. |
| 2015/0289925 A1 | 10/2015 | Voegele et al. |
| 2015/0297286 A1 | 10/2015 | Boudreaux et al. |
| 2016/0045248 A1 | 2/2016 | Unger et al. |
| 2016/0051315 A1 | 2/2016 | Boudreaux |
| 2016/0051316 A1 | 2/2016 | Boudreaux |
| 2016/0051317 A1 | 2/2016 | Boudreaux |
| 2016/0058492 A1 | 3/2016 | Yates et al. |
| 2016/0074108 A1 | 3/2016 | Woodruff et al. |
| 2016/0128762 A1 | 5/2016 | Harris et al. |
| 2016/0135875 A1 | 5/2016 | Strobl et al. |
| 2016/0157927 A1 | 6/2016 | Corbett et al. |
| 2016/0175024 A1 | 6/2016 | Yates et al. |
| 2016/0175028 A1 | 6/2016 | Trees et al. |
| 2016/0175029 A1 | 6/2016 | Witt et al. |
| 2016/0175030 A1 | 6/2016 | Boudreaux |
| 2016/0175031 A1 | 6/2016 | Boudreaux |
| 2016/0175032 A1 | 6/2016 | Yang |
| 2016/0199123 A1 | 7/2016 | Thomas et al. |
| 2016/0199125 A1 | 7/2016 | Jones |
| 2016/0228171 A1 | 8/2016 | Boudreaux |
| 2016/0270840 A1 | 9/2016 | Yates et al. |
| 2016/0270841 A1 | 9/2016 | Strobl et al. |
| 2016/0270842 A1 | 9/2016 | Strobl et al. |
| 2016/0270843 A1 | 9/2016 | Boudreaux et al. |
| 2016/0278848 A1 | 9/2016 | Boudreaux et al. |
| 2016/0296268 A1 | 10/2016 | Gee et al. |
| 2016/0296270 A1 | 10/2016 | Strobl et al. |
| 2016/0296271 A1 | 10/2016 | Danziger et al. |
| 2016/0302844 A1 | 10/2016 | Strobl et al. |
| 2016/0317215 A1 | 11/2016 | Worrell et al. |

FOREIGN PATENT DOCUMENTS

| | | |
|---|---|---|
| DE | 19608716 C1 | 4/1997 |
| DE | 29623113 U1 | 10/1997 |
| DE | 20004812 U1 | 9/2000 |
| DE | 10201569 A1 | 7/2003 |
| EP | 0340803 B1 | 8/1993 |
| EP | 0630612 A1 | 12/1994 |
| EP | 0705571 A1 | 4/1996 |
| EP | 0557806 B1 | 5/1998 |
| EP | 0640317 B1 | 9/1999 |
| EP | 0722696 B1 | 12/2002 |
| EP | 1293172 B1 | 4/2006 |
| EP | 0875209 B1 | 5/2006 |
| EP | 1704824 A1 | 9/2006 |
| EP | 1749479 A1 | 2/2007 |
| EP | 1767157 A1 | 3/2007 |
| EP | 1254637 B1 | 8/2007 |
| EP | 1878399 A1 | 1/2008 |
| EP | 1915953 A1 | 4/2008 |
| EP | 1532933 B1 | 5/2008 |
| EP | 1707143 B1 | 6/2008 |
| EP | 1943957 A2 | 7/2008 |
| EP | 1435852 B1 | 12/2008 |
| EP | 1849424 B1 | 4/2009 |
| EP | 2042117 A1 | 4/2009 |
| EP | 1810625 B1 | 8/2009 |
| EP | 2060238 A1 | 8/2009 |
| EP | 2090238 A1 | 8/2009 |
| EP | 2090256 A2 | 8/2009 |
| EP | 2092905 A1 | 8/2009 |
| EP | 2105104 A2 | 9/2009 |
| EP | 1747761 B1 | 10/2009 |
| EP | 1769766 B1 | 2/2010 |
| EP | 2151204 A1 | 2/2010 |
| EP | 2153791 A1 | 2/2010 |
| EP | 2243439 A1 | 10/2010 |
| EP | 1510178 B1 | 6/2011 |
| EP | 1728475 B1 | 8/2011 |
| EP | 2353518 A1 | 8/2011 |
| EP | 2529681 A1 | 12/2012 |
| EP | 1767164 B1 | 1/2013 |
| EP | 2316359 B1 | 3/2013 |
| EP | 2578172 A2 | 4/2013 |
| EP | 2508143 B1 | 2/2014 |
| GB | 2472216 A | 2/2011 |
| JP | H08-229050 A | 9/1996 |
| JP | 2008-018226 A | 1/2008 |
| JP | 5714508 B2 | 5/2015 |
| WO | WO 81/03272 A1 | 11/1981 |
| WO | WO 93/07817 A1 | 4/1993 |
| WO | WO 93/22973 A1 | 11/1993 |
| WO | WO 95/10978 A1 | 4/1995 |
| WO | WO 96/35382 A1 | 11/1996 |
| WO | WO 97/10764 A1 | 3/1997 |
| WO | WO 98/00069 A1 | 1/1998 |
| WO | WO 98/40020 A1 | 9/1998 |
| WO | WO 98/57588 A1 | 12/1998 |
| WO | WO 99/23960 A1 | 5/1999 |
| WO | WO 99/40857 A1 | 8/1999 |
| WO | WO 99/40861 A1 | 8/1999 |
| WO | WO 00/24330 A1 | 5/2000 |
| WO | WO 00/24331 A1 | 5/2000 |
| WO | WO 00/25691 A1 | 5/2000 |
| WO | WO 01/28444 A1 | 4/2001 |
| WO | WO 02/062241 A1 | 8/2002 |
| WO | WO 02/080797 A1 | 10/2002 |
| WO | WO 03/001986 A2 | 1/2003 |

(56) References Cited

FOREIGN PATENT DOCUMENTS

| WO | WO 03/013374 A1 | 2/2003 |
|---|---|---|
| WO | WO 03/020339 A2 | 3/2003 |
| WO | WO 03/028541 A2 | 4/2003 |
| WO | WO 03/030708 A2 | 4/2003 |
| WO | WO 03/068046 A2 | 8/2003 |
| WO | WO 2004/011037 A2 | 2/2004 |
| WO | WO 2004/032754 A2 | 4/2004 |
| WO | WO 2004/032762 A1 | 4/2004 |
| WO | WO 2004/032763 A2 | 4/2004 |
| WO | WO 2004/078051 A2 | 9/2004 |
| WO | WO 2004/112618 A2 | 12/2004 |
| WO | WO 2005/052959 A2 | 6/2005 |
| WO | WO 2006/021269 A1 | 3/2006 |
| WO | WO 2006/036706 A1 | 4/2006 |
| WO | WO 2006/055166 A2 | 5/2006 |
| WO | WO 2006/119139 A2 | 11/2006 |
| WO | WO 2008/020964 A2 | 2/2008 |
| WO | WO 2008/045348 A2 | 4/2008 |
| WO | WO 2008/099529 A1 | 8/2008 |
| WO | WO 2008/101356 A1 | 8/2008 |
| WO | WO 2009/022614 A1 | 2/2009 |
| WO | WO 2009/036818 A1 | 3/2009 |
| WO | WO 2009/039179 A1 | 3/2009 |
| WO | WO 2009/059741 A1 | 5/2009 |
| WO | WO 2009/082477 A2 | 7/2009 |
| WO | WO 2009/149234 A1 | 12/2009 |
| WO | WO 2010/017266 A1 | 2/2010 |
| WO | WO 2010/104755 A1 | 9/2010 |
| WO | WO 2011/008672 A2 | 1/2011 |
| WO | WO 2011/084768 A1 | 7/2011 |
| WO | WO 2011/089717 A1 | 7/2011 |
| WO | WO 2011/144911 A1 | 11/2011 |
| WO | WO 2012/044606 A2 | 4/2012 |
| WO | WO 2012/166510 A1 | 12/2012 |
| WO | WO 2013/034629 A1 | 3/2013 |
| WO | WO 2013/062978 A2 | 5/2013 |
| WO | WO 2013/102602 A2 | 7/2013 |
| WO | WO 2013/154157 A1 | 10/2013 |
| WO | WO 2015/197395 A8 | 12/2015 |

OTHER PUBLICATIONS

Hörmann et al., "Reversible and irreversible denaturation of collagen fibers." Biochemistry, 10, pp. 932-937 (1971).
Henriques. F.C., "Studies in thermal injury V. The predictability and the significance of thermally induced rate processes leading to irreversible epidermal injury." Archives of Pathology, 434, pp. 489-502 (1947).
Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
Chen et al., "Heat-induced changes in the mechanics of a collagenous tissue: pseudoelastic behavior at 37° C," Journal of Biomechanics, 31, pp. 211-216 (1998).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . ., accessed Aug. 25, 2009.
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wall et al., "Thermal modification of collagen," J Shoulder Elbow Surg, No. 8, pp. 339-344 (Jul./Aug. 1999).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Humphrey, J.D., "Continuum Thermomechanics and the Clinical Treatment of Disease and Injury," Appl. Mech. Rev., vol. 56, No. 2 pp. 231-260 (Mar. 2003).
Kurt Gieck & Reiner Gieck, *Engineering Formulas* § Z.7 (7th ed. 1997).
National Semiconductors Temperature Sensor Handbook—http://www.national.com/appinfo/tempsensors/files/temphb.pdf; accessed online: Apr. 1, 2011.
Glaser and Subak-Sharpe, *Integrated Circuit Engineering*, Addison-Wesley Publishing, Reading, MA (1979). (book—not attached).
Wright, et al., "Time-Temperature Equivalence of Heat-Induced Changes in Cells and Proteins," Feb. 1998. ASME Journal of Biomechanical Engineering, vol. 120, pp. 22-26.
Covidien Brochure, [Value Analysis Brief], LigaSure Advance™ Pistol Grip, dated Rev. Apr. 2010 (7 pages).
Covidien Brochure, LigaSure Impact™ Instrument LF4318, dated Feb. 2013 (3 pages).
Covidien Brochure, LigaSure Atlas™ Hand Switching Instruments, dated Dec. 2008 (2 pages).
Covidien Brochure, The LigaSure™ 5 mm Blunt Tip Sealer/Divider Family, dated Apr. 2013 (2 pages).
Covidien Brochure, The LigaSure Precise™ Instrument, dated Mar. 2011 (2 pages).
Erbe Electrosurgery VIO® 200 S, (2012), p. 7, 12 pages, accessed Mar. 31, 2014 at http://www.erbe-med.com/erbe/media/Marketingmaterialien/85140-170_ERBE_EN_VIO_200_S_D027541.
Jang, J. et al. "Neuro-fuzzy and Soft Computing." Prentice Hall, 1997, pp. 13-89, 199-293, 335-393, 453-496, 535-549.
Douglas, S.C. "Introduction to Adaptive Filter". Digital Signal Processing Handbook. Ed. Vijay K. Madisetti and Douglas B. Williams. Boca Raton: CRC Press LLC, 1999.
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Sullivan, "Optimal Choice for Number of Strands in a Litz-Wire Transformer Winding," IEEE Transactions on Power Electronics, vol. 14, No. 2, Mar. 1999, pp. 283-291.
https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.
U.S. Appl. No. 12/576,529, filed Oct. 9, 2009.
U.S. Appl. No. 15/265,293, filed Sep. 14, 2016.
U.S. Appl. No. 15/258,570, filed Sep. 7, 2016.
U.S. Appl. No. 15/258,578, filed Sep. 7, 2016.
U.S. Appl. No. 15/258,586, filed Sep. 7, 2016.
U.S. Appl. No. 15/258,598, filed Sep. 7, 2016.
International Preliminary Report on Patentability for PCT/US2015/025893 dated Oct. 18, 2016 (10 pages).
International Search Report for PCT/US2015/025893 dated Jul. 21, 2015 (5 pages).

\* cited by examiner

DEVICE STATUS FEEDBACK FOR BIPOLAR TISSUE SPACER

BACKGROUND

The present invention relates to surgical instruments and, in various circumstances, to surgical sealing and transecting instruments.

BRIEF DESCRIPTION OF THE DRAWINGS

The features and advantages of this invention, and the manner of attaining them, will become more apparent and the invention itself will be better understood by reference to the following description of instances of the invention taken in conjunction with the accompanying drawings, wherein.

DETAILED DESCRIPTION

Figure 1:
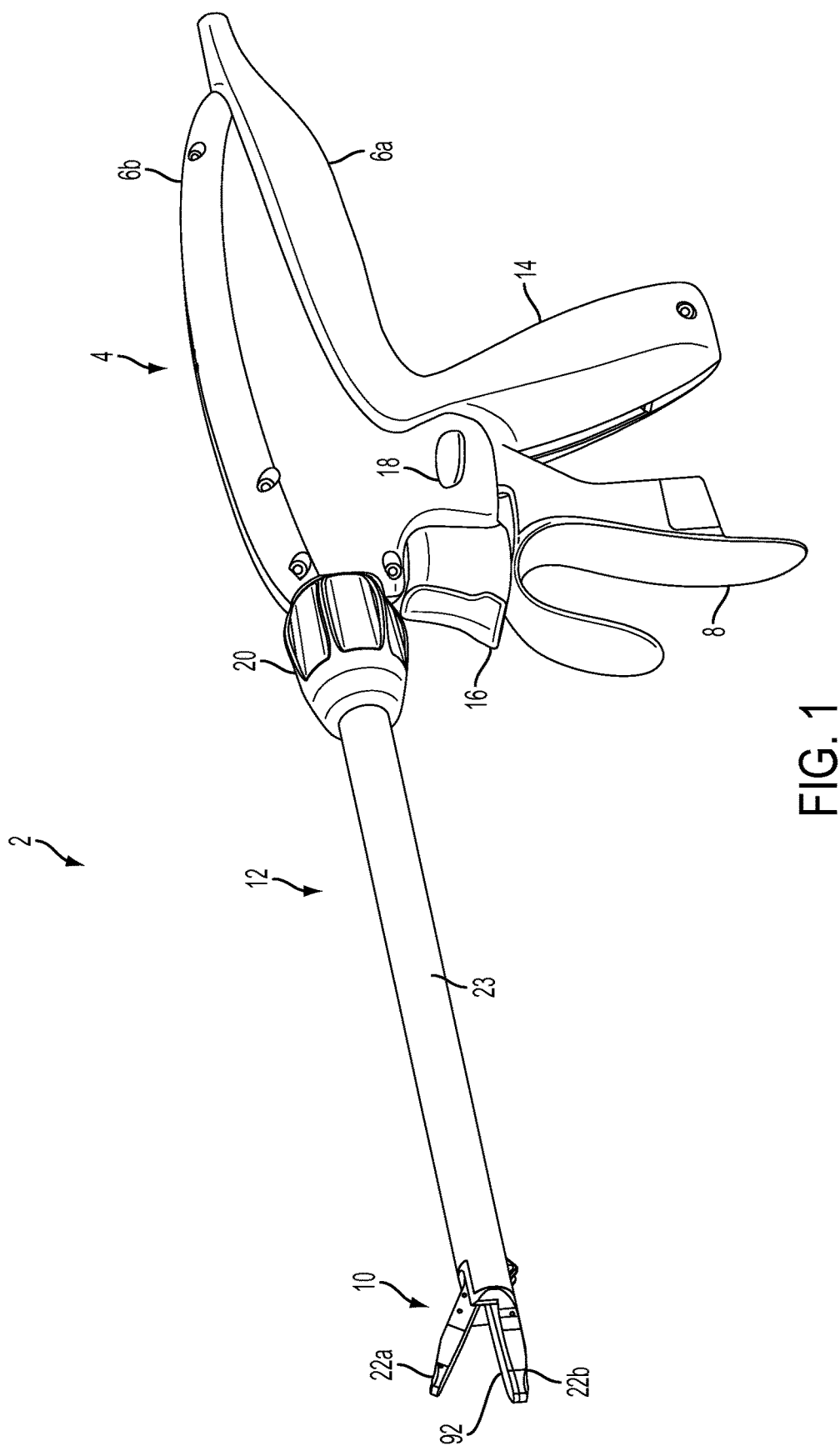
FIG. 1 illustrates a perspective view of a surgical instrument comprising a handle and an end effector assembly.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the person of ordinary skill in the art will readily appreciate that the various methods and devices disclosed herein can be used in numerous surgical procedures and applications including, for example, in connection with open surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongated shaft of a surgical instrument can be advanced.

Turning to the Drawings wherein like numerals denote like components throughout the several views, FIG. 1 depicts one form of an electrosurgical instrument 2. The electrosurgical instrument 2 comprises a handle assembly 4, a shaft assembly 12 coupled to a distal end of the handle assembly 4, and an end effector 10 coupled to the distal end of the shaft assembly 12. The handle assembly 4 is configured as a pistol grip and comprises left and right handle housing shrouds 6a, 6b, a closure trigger 8, a pistol-grip handle 14, a firing trigger 16, an energy button 18, and a rotatable shaft knob 20. An electrical cable may enter the handle assembly 4 at a proximal end.

In some circumstances, the end effector 10 can be coupled to the distal end of the shaft assembly 12. The end effector 10 may include a first jaw 22a and a second jaw 22b. The first jaw 22a is pivotably coupled to the second jaw 22b. The first jaw 22a is pivotally moveable with respect to the second jaw 22b to grasp tissue therebetween. In some circumstances, the second jaw 22b is fixed. In other circumstances, the first jaw 22a and the second jaw 22b are pivotally movable. The end effector 10 may include at least one electrode 92. The electrode 92 is configured to deliver energy. Energy delivered by the electrode 92 may comprise, for example, radiofrequency (RF) energy, sub-therapeutic RF energy, ultrasonic energy, and/or other suitable forms of energy. In some circumstances, a cutting member (not shown) is receivable within a longitudinal slot defined by the first jaw 22a and/or the second jaw 22b. The cutting member can be configured to cut tissue grasped between the first jaw 22a and the second jaw 22b. In some circumstances, the cutting member may include an electrode for delivering energy, such as, for example, RF and/or ultrasonic energy.

In certain instances, an energy button 18 is configured to deliver energy to the at least one electrode 92 coupled to the end effector 10 from a power source. In certain instances, when the energy button 18 is depressed, a circuit is completed allowing delivery of energy to the electrode 92. In some embodiments, the power source is a generator. In certain instances, the generator is external to the surgical instrument 2 which is separably coupled to the generator. In other instances, the generator is integrated with the surgical instrument 2. In certain instances, feedback systems described by the present disclosure comprise indicators which are housed within the generator and can be separably coupled to the surgical instrument 2 in the instances where the generator is separably coupled to the surgical instrument 2, for example. In certain instances, the power source may be suitable for therapeutic tissue treatment, tissue cauterization/sealing, as well as sub-therapeutic treatment and measurement.

In certain instances, the surgical instrument 2 may include a closure drive assembly which may comprise an outer sheath 23, for example. In certain instances, the closure trigger 8 can be operatively coupled to at least one of the jaws 22a, 22b through the closure drive assembly such that actuation of the closure trigger 8 in a closure stroke may transition the jaws 22a, 22b between a plurality of configurations including an open configuration and an approximated configuration, for example. In certain instances, the surgical instrument 2 may include a firing drive assembly. In certain instances, the firing trigger 16 may be operatively coupled to the cutting member of the end effector 10 through the firing drive assembly such that actuation of the firing trigger 16 in a firing stroke may cause the cutting member to be advanced relative to the end effector 10 to cut tissue captured between the jaws 22a, 22b, for example.

Figure 2:
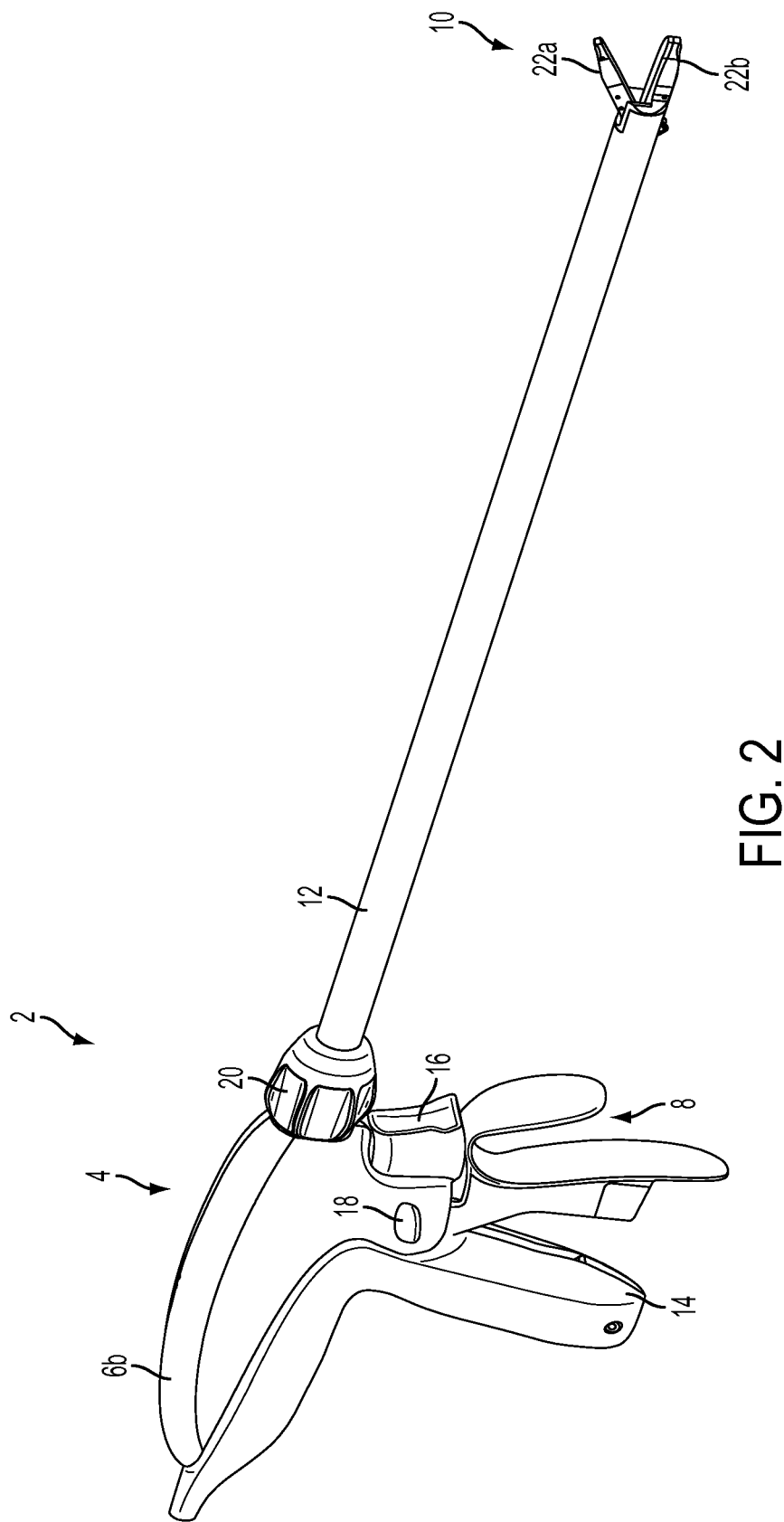
FIG. 2 illustrates a perspective view of the surgical instrument of FIG. 1.
Figure 3:
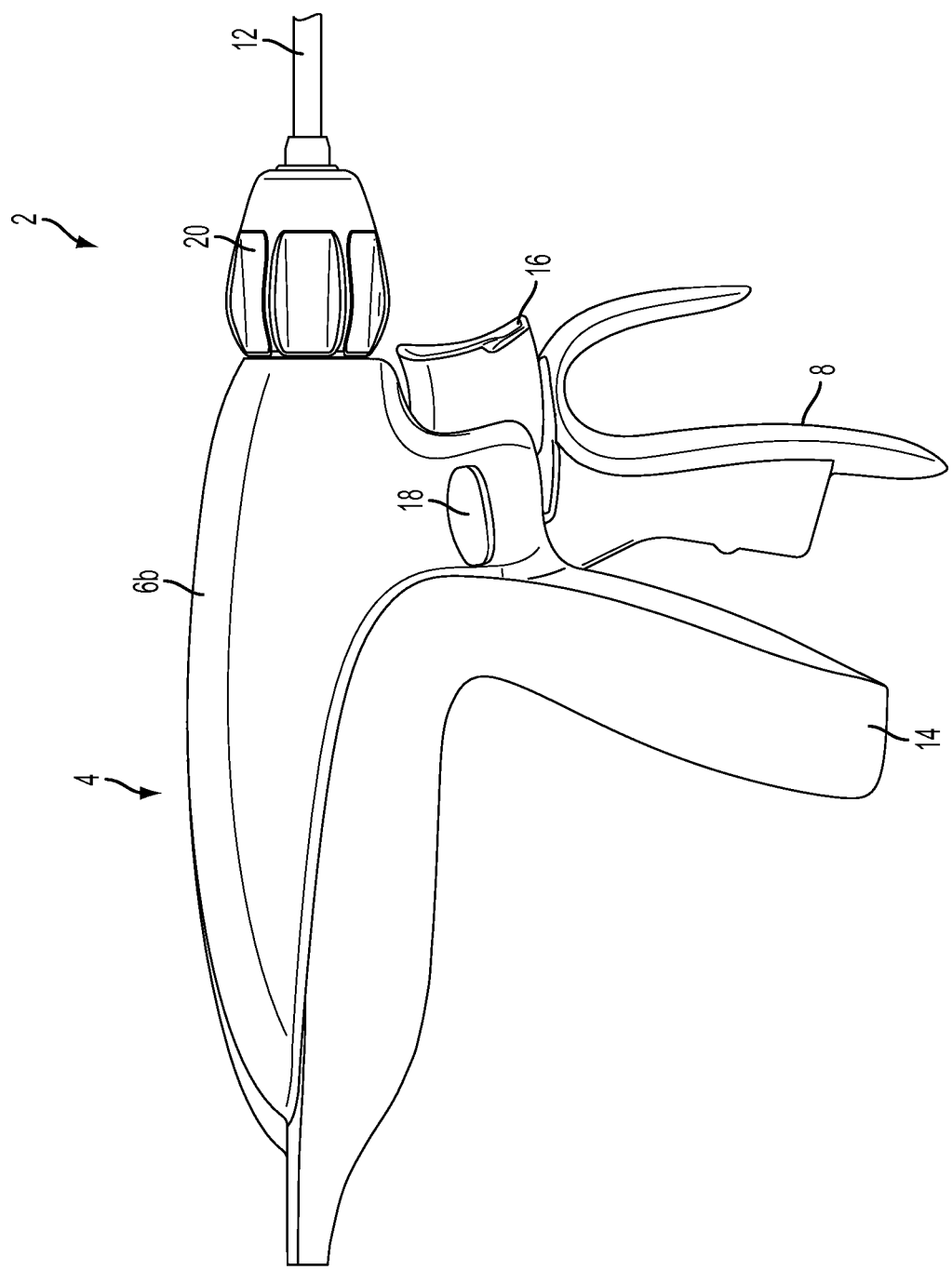
FIG. 3 illustrates a partial side view of the surgical instrument of FIG. 1.

FIG. 2 illustrates a side perspective view of the electrosurgical instrument 2 illustrated in FIG. 1. FIG. 2 illustrates the right handle housing 6b. The energy button 18 extends through the handle assembly 4 and is accessible on both sides of the handle assembly 4. The closure trigger 8, the firing trigger 16, and the energy button 18 may comprise an ergonomic design. In some circumstances, the handle assembly 4 is thinner near the energy button 18 to allow ease of access to the energy button 18 by a clinician. In some circumstances, the energy button 18 is disposed on either the left handle housing 6a or the right handle housing 6b. FIG. 3 illustrates a side view of the electrosurgical instrument 2 and the right handle housing 6b. Various electrosurgical instruments suitable for use with the present disclosure are described in U.S. patent application Ser. Nos. 14/075,839 and 14/075,863. U.S. patent application Ser. No. 14/075, 839, entitled ELECTROSURGICAL DEVICES, and filed Nov. 8, 2013, is hereby incorporated by reference herein in its entirety. Furthermore, U.S. patent application Ser. No. 14/075,863, entitled ELECTROSURGICAL DEVICES, and filed Nov. 8, 2013, is hereby incorporated by reference herein in its entirety.

Figure 4:
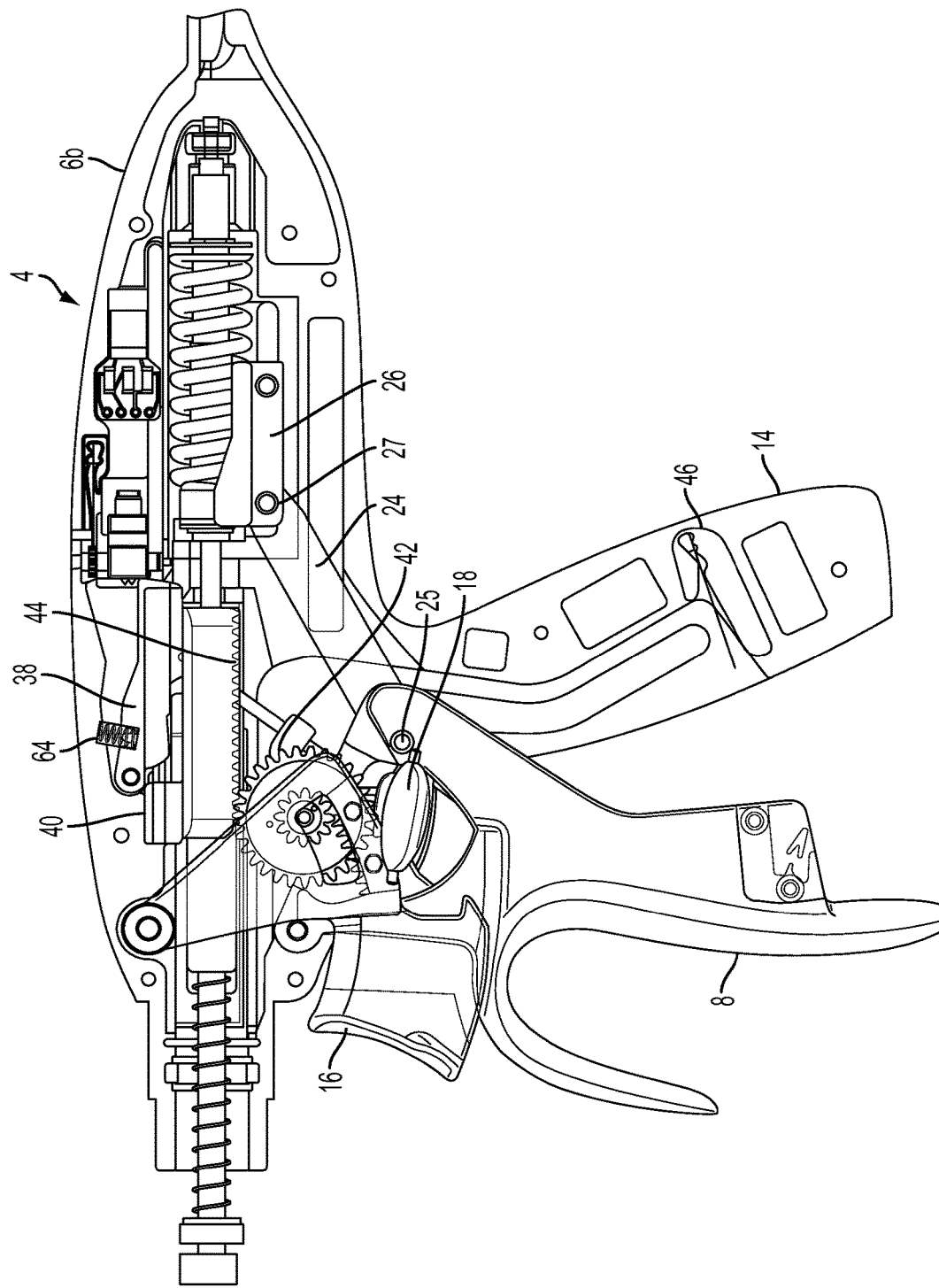
FIG. 4 illustrates a partial side view of a handle assembly of the surgical instrument of FIG. 1 with a removed housing shroud.

FIG. 4 illustrates one embodiment of the surgical instrument 2 of FIG. 1 with the left handle housing 6a removed. The handle assembly 4 comprises a plurality of components for actuating the surgical instrument 2, such as, for example, mechanisms for affecting closure of the jaws 22a, 22b of the end effector 10, deploying the cutting member within the end effector 10, and/or delivering energy to the one or more electrodes 92 coupled to the end effector 10. In certain instances, a closure trigger 8 may be operably coupled to a closure drive assembly which can be configured to transition the jaws 22a, 22b between an open configuration and an approximated configuration. In certain instances, the closure trigger 8 is connected to a closure actuator located within the handle assembly 4. In certain instances, the closure actuator comprises a toggle arm 24 which may be coupled to the closure trigger 8 at a first pivot 25 and to a yoke 26 at a second pivot 27. In certain instances, the closure actuator may comprise any suitable actuator for coupling the closure trigger 8 to a jaw actuator of the shaft assembly. For example, in some embodiments, the closure actuator comprises an L-shaped lever arm. In certain instances, when the closure trigger 8 is actuated towards the pistol grip handle 14, the toggle arm 24 may drive movement of the yoke 26 in a first direction along a longitudinal axis L-L. Longitudinal movement of the yoke 26 in the first direction may drive a closure drive, such as, for example, the outer sheath 23, to transition the jaws 22a, 22b from the open configuration to the approximated configuration, for example. Furthermore, the longitudinal movement of the yoke 26 in a second direction, opposite the first direction, may drive the closure drive to transition the jaws 22a, 22b from the approximated configuration to the open configuration, for example.

In certain instances, a firing trigger 16 is configured to deploy the cutting member within the end effector 10. The firing trigger 16 can be operatively coupled to firing drive assembly including, for example, a compound gear 42, as illustrated in FIG. 4. The compound gear 42 may interface with a rack 44, for example. The rack 44 can be coupled to a firing drive which may extend through the outer sheath 23 and may transmit axial motions to the cutting member of the end effector 10. In certain instances, when the firing trigger 16 is actuated, the compound gear 42 rotates and moves the rack 44 distally. The distal movement of the rack 44 may cause distal movement of the firing drive and deployment of the cutting member within the end effector 10. The cutting member can be deployed from a proximal end of the end effector 10 to a distal end of the end effector 10. In certain instances, the firing trigger 16 comprises a high pivot to provide a linear feel during actuation of the firing trigger 16. The linear feel provides increased control and comfort to a clinician actuating the firing trigger 16.

In certain instances, the compound gear 42 can be operably coupled to a motor (not shown). Rotational motions generated by the motor may cause the rack 44 to be advanced distally, and in turn cause the cutting member to be deployed from the proximal end of the end effector 10 to the distal end of the end effector 10, for example. In certain instances, the motor can be powered by a power source such as, for example, a battery (not shown). In certain instances, the firing trigger 16 may comprise a switch (not shown), for example, which can be operably coupled to a circuit, for example, such that movement of the firing trigger 16 from a first position to a second position may cause the switch to close the circuit which may activate the motor to deploy the cutting member, for example.

Figure 5:
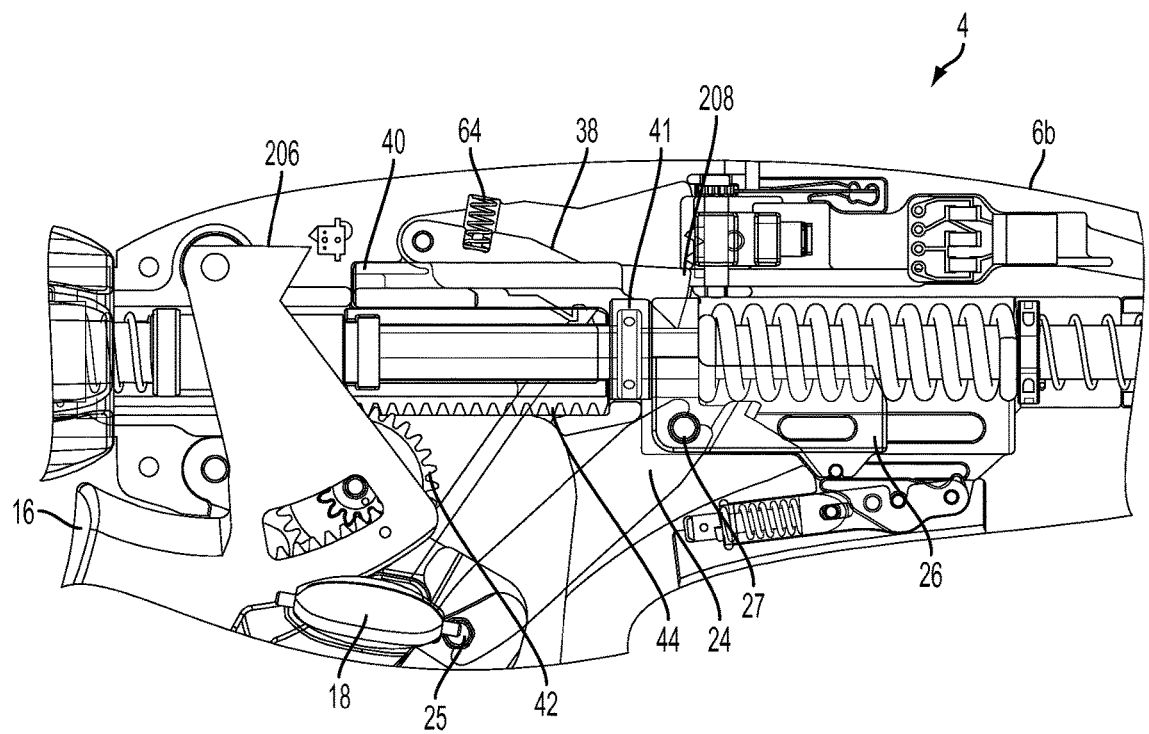
FIG. 5 illustrates a partial side view of a handle assembly of the surgical instrument of FIG. 1 with a removed housing shroud.

Referring to FIGS. 4 and 5, in some instances, the surgical instrument 2 may comprise a locking mechanism which may be configured to engage the firing drive assembly to interfere with, resist, and/or prevent deployment of the cutting member of the end effector 10. In certain instances, the locking mechanism may include a locking member 38. In certain instances, the locking member 38 can be transitioned between a locked configuration and an unlocked configuration; in the locked configuration, the locking member 38 can be configured to engage a rack unlock block 40 of the firing drive assembly to interfere with, resist, and/or prevent deployment of the cutting member of the end effector 10. In certain instances, as illustrated in FIG. 5, a lock spring 64 may be coupled to the locking member 38 to apply a biasing force against the locking member 38. The biasing force may bias the locking member 38 to maintain a locking engagement with the firing drive assembly.

Figure 7:
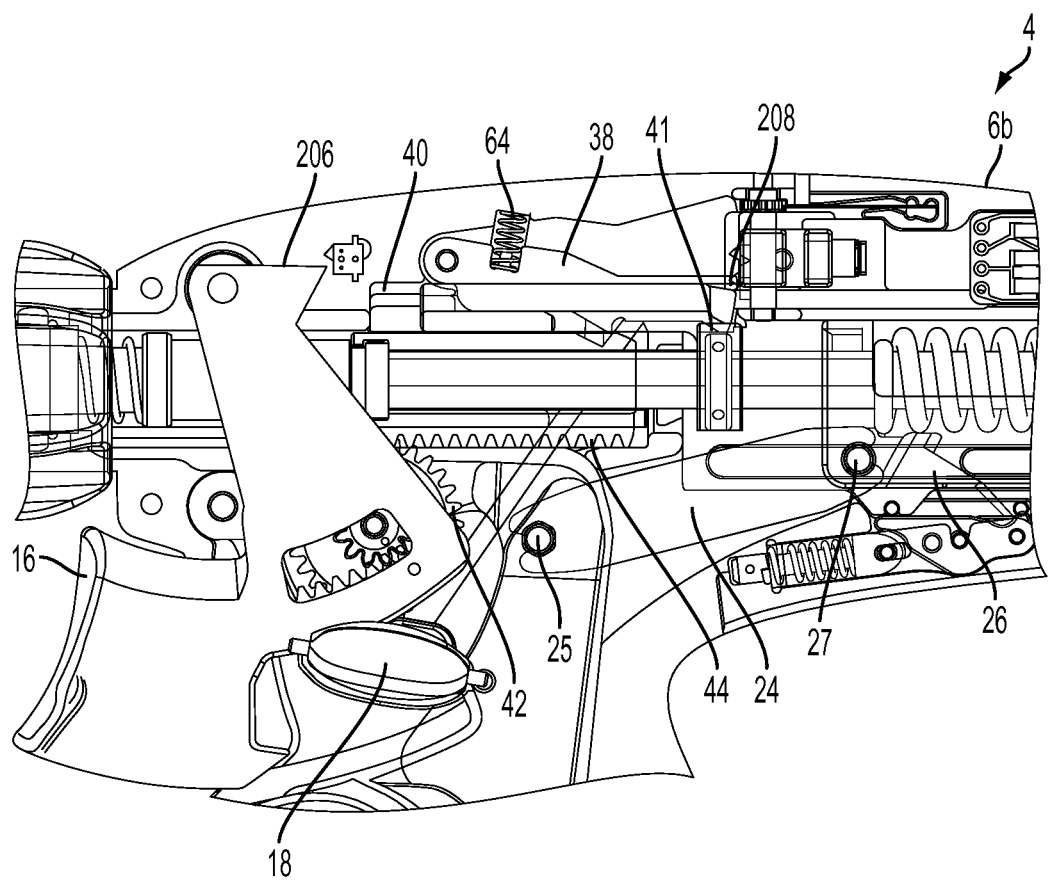
FIG. 7 illustrates a partial side view of a handle assembly of the surgical instrument of FIG. 1 with a removed housing shroud.

In certain instances, the closure drive assembly is movable to release the firing drive assembly by causing the locking member 38 to transition from locking engagement with the rack unlock block 40, as illustrated in FIG. 5, to the unlocked configuration, as illustrated in FIG. 7, for example. In certain instances, the closure drive assembly may comprise an unlocking member 41 which may be movable to raise the locking member 38 from locking engagement with the rack unlock block 40, for example. In other words, actuation of the trigger 8 may transition the jaw 22a, 22b to the approximated configuration and may release the locking mechanism of the firing drive assembly by causing the unlocking member 41 to motivate the locking member 38 out of locking engagement with the rack unlock block 40, for example. In certain instances, when the closure trigger 8 is released and the yoke 26 returns to a rest position, the lock spring 64 may bias the locking member 38 back into a locking engagement with the rack unlock block 40, for example.

In certain instances, the locking mechanism of the surgical instrument 2 may be employed as a safety mechanism which may prevent deployment of the cutting member of the end effector 10 while the jaws 22a, 22b are in the open configuration and/or while the jaws 22a, 22b are not sufficiently transitioned to the closed configuration. In use, a clinician may orient the end effector 10 to position the jaws 22a, 22b around a desired tissue to seal and cut the desired tissue. Furthermore, the clinician may actuate the closure trigger 8 to transition the jaws 22a, 22b from the open configuration toward the approximated configuration to clamp the desired tissue, for example. In certain instances, however, the surgical instrument 2 may not be appropriate for safely treating the clamped tissue. For example, the clamped tissue may comprise a thickness that is too large to be safely treated with the surgical instrument 2. In such instances, the locking mechanism may be employed to prevent deployment of the cutting member of the end effector 10 to cut the clamped tissue if the clinician actuates the firing trigger 16 to deploy the cutting member to cut the clamped tissue. In other words, the thickness of the clamped tissue may not permit sufficient closure of the jaws 22a, 22b around the clamped tissue for the jaws 22a, 22b to reach the approximated configuration. Accordingly, the clinician may not be able to sufficiently actuate the closure trigger 8 to complete a closure stroke. In turn, the unlocking member 41 may not be sufficiently motivated to release the locking member 38 out of locking engagement with the rack unlock block 40.

In certain instances, the yoke 26 can be coupled to an unlocking member 41. In certain instances, when the yoke 26 is moved in response to the actuation of the closure trigger 8, the locking member 41 lifts the locking member 38 vertically away from the rack unlock block 40. In certain instances, when the locking member 38 has been lifted a sufficient distance, the rack 44 is allowed to move and the firing trigger 16 is actuatable to deploy the cutting member within the end effector 10. In certain instances, the firing trigger 16 is unlocked when the jaws 22a, 22b are sufficiently closed such that the cutting member cannot skip out of a slot formed in the end effector 10. For example, in some instances, the locking member 38 is released when the closure trigger 8 is rotated about 30 degrees. In other instances, the locking member 38 may be released at a lower or higher degree of rotation of the closure trigger 8. In certain instances, the firing trigger 16 is unlocked when the clamped tissue between the jaws 22a, 22b is sufficiently compressed to enable the cutting member to fully transect the clamped tissue. In certain instances, the firing trigger 16 is unlocked when the clamped tissue between the jaws 22a, 22b is sufficiently compressed to a thickness that is less than or equal, or at least substantially equal, to the height of the cutting surface of the cutting member of the end effector 10, for example.

The reader will appreciate that it may be desirable to provide a clinician utilizing the surgical instrument 2 with feedback at various stages during operation of the surgical instrument 2. In certain instances, the surgical instrument 2 may comprise one or more mechanical feedback systems. In certain instances, the surgical instrument 2 may comprise one or more electrical feedback systems. In certain instances, the surgical instrument 2 may comprise combinations of mechanical feedback systems and electrical feedback systems. In certain instances, some of the feedback systems described herein may include one or more indicators. In certain instances, the indicators may comprise, for example, visual indicators such as display screens, backlights, and/or LEDs, for example. In certain instances, the indicators may comprise audio indicators such as speakers and/or buzzers, for example. In certain instances, the indicators may comprise tactile indicators such as haptic actuators, for example. In certain instances, the indicators may comprise combinations of visual indicators, audio indicators, and/or tactile indicators, for example.

In certain instances, one or more of the feedback systems of the surgical instrument 2 may be configured to alert a clinician actuating the closure trigger 8 if a tissue bite clamped by the end effector 10 comprises a thickness that is too large for proper treatment via the surgical instrument 2. In certain instances, one or more of the feedback systems of the surgical instrument 2 may be configured to alert a clinician actuating the firing trigger 16 if the firing drive assembly is locked by the locking mechanism of the surgical instrument 2. For example, the one or more of the feedback systems of the surgical instrument 2 may be configured to alert the clinician actuating the firing trigger 16 if the locking member 38 is in locking engagement with the rack unlock block 40. In certain instances, one or more of the feedback systems of the surgical instrument 2 may be configured to alert a clinician actuating the closure trigger 8 when the firing drive assembly becomes unlocked. In other words, one or more of the feedback systems of the surgical instrument 2 may be configured to alert a clinician actuating the closure trigger 8 when the jaws 22a, 22b are sufficiently closed such that the rack unlock block 40 is released from locking engagement with locking member 38.

Figure 5A:
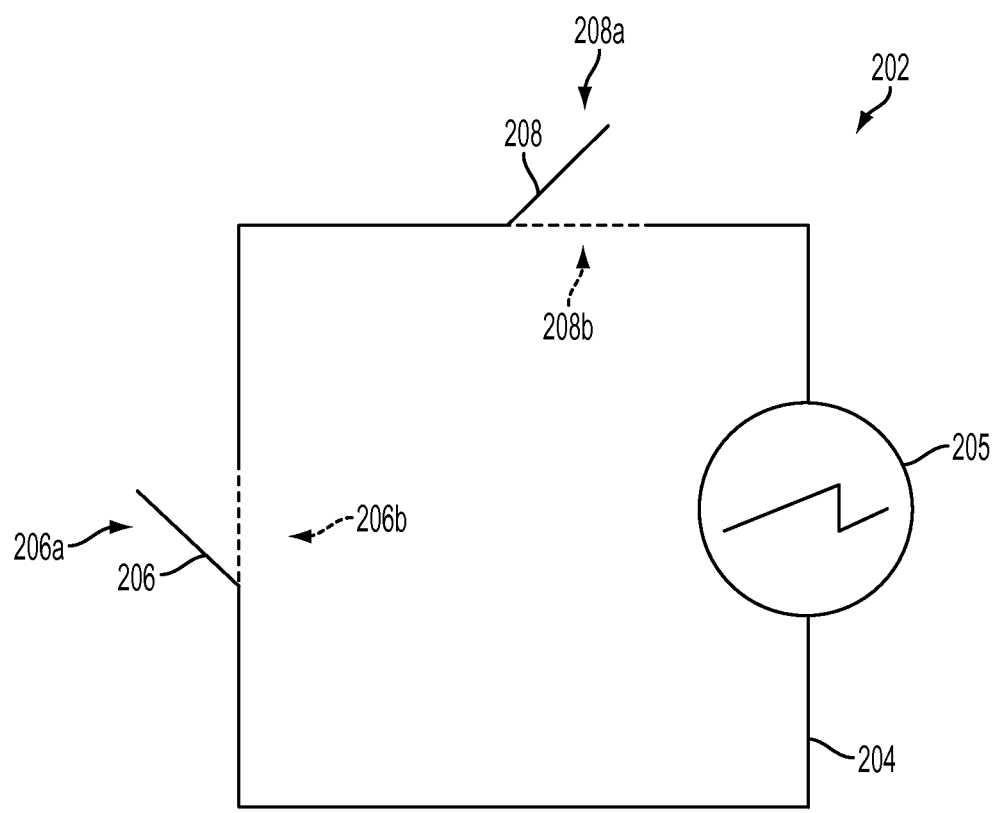
FIG. 5A illustrates a feedback system including an indicator circuit for use with the surgical instrument of FIG. 1.
Figure 6:
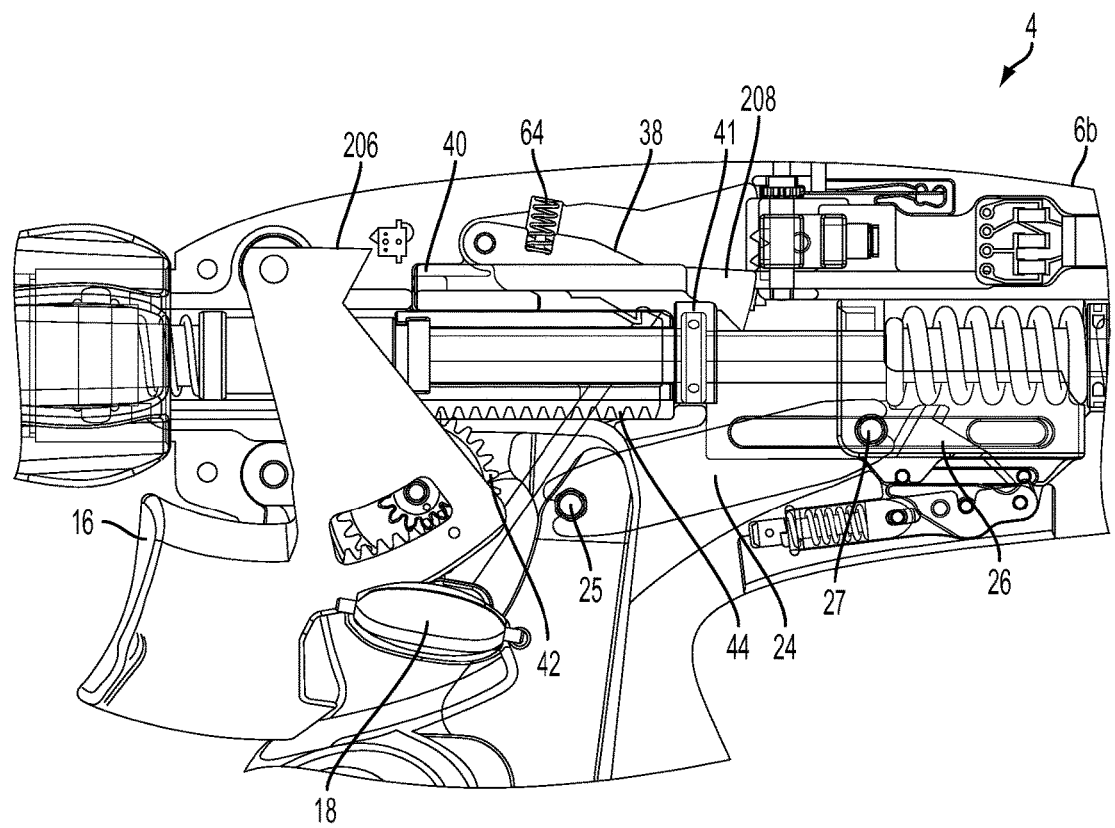
FIG. 6 illustrates a partial side view of a handle assembly of the surgical instrument of FIG. 1 with a removed housing shroud.

Referring to FIGS. 5-7, the surgical instrument 2 may comprise an electrical feedback system 202 (FIG. 5A). In certain instances, the system 202 may include an indicator circuit 204 which may comprise an indicator 205. In certain instances, the circuit 204 may include a plurality of switches such as, for example, normally open, normally closed, and/or other switch types. In certain instances, the circuit 204 may include a switch 206 which may be associated with the firing trigger 16, for example. In certain instances, as illustrated in FIG. 5A, the switch 206 can be transitioned between an inactive or open configuration or position 206a and an active or closed configuration or position 206b. In certain instances, the switch 206 can be coupled to the firing trigger 16 such that actuation of the firing trigger 16 between an unactuated position and a first actuated position during the firing stroke may cause the switch 206 to move from the inactive configuration 206a to the active configuration 206b. In certain instances, the actuation of the firing trigger 16 from the unactuated position to the first actuated position may be a slight actuation that may not cause movement of the cutting member of the end effector 10 or may cause a slight movement of the cutting member of the end effector 10 that may not cause the cutting member to be sufficiently advanced to cut tissue clamped between the jaws 22a, 22b.

Referring again to FIGS. 5-7, in certain instances, the circuit 204 may include a switch 208 which may be associated with the locking member 38, for example. In certain instances, as illustrated in FIG. 5A, the switch 208 can be transitioned between an inactive or open configuration or position 208a and an active or closed configuration or position 208b.

As described above, the locking member 38 can be transitioned between the locked position, wherein the locking member 38 is in locking engagement with the firing drive assembly, and the unlocked position, wherein firing drive assembly is released from locking engagement with the locking member 38. In certain instances, the switch 208 can be coupled to the locking member 38 such that the switch 208 remains in the active configuration 208b while the locking member 38 is in the locked configuration. Furthermore, the switch 208 may be transitioned from the active configuration 208b to the inactive configuration 208a when the locking member 38 is transitioned from the locked configuration to the unlocked configuration, for example.

Referring primarily to FIG. 5A, in certain instances, the indicator circuit 204 is closed and the indicator 205 is activated when the switch 206 and the switch 208 are both in the active configuration, for example. In certain instances, the indicator circuit 204 is open and the indicator 205 is inactive if one of the switch 206 and the switch 208 is in the inactive configuration, for example. In certain instances, the indicator circuit 204 is open and the indicator 205 is inactive if both of the switches 206 and 208 are in the inactive configuration, for example.

In certain instances, when the locking member 38 is in the locked configuration and the firing trigger 16 is in the first actuated position, the indicator circuit 204 is closed and the indicator 205 is activated. For example, a clinician may actuate the closure trigger 8 to clamp tissue comprising a thickness that is too large for proper treatment via the surgical instrument 2. In such instances, the locking member 38 may remain in the locked configuration because the unlocking member 41 has not been sufficiently moved by the closure trigger 8 to separate the locking member 38 from locking engagement with the firing drive assembly, as described above. In result, the switch 208 may remain in the active configuration 208b. In such instance, if the clinician attempts to actuate the firing trigger 16 from the unactuated position to the first actuated position, as described above, the switch 206 may also be transitioned to the active configuration 206b which may cause the indicator circuit 204 to be closed and the indicator 205 to be activated to alert the clinician that the cutting member cannot be advanced to cut tissue captured by the end effector 10 because the firing drive assembly is locked, for example. In other words, the indicator 205 may alert the clinician that the jaws 22a, 22b are too far apart and that the cutting member cannot be advanced. In response, the clinician may release the captured tissue and may attempt to capture a more suitable tissue target, for example.

The reader will appreciate that if the captured tissue is not too large for proper treatment with the surgical instrument 2, the closure trigger 8 may be sufficiently actuated to allow the unlocking member 41 to sufficiently motivate the locking member 38 to the unlocked configuration to release the rack unlock block 40 and free the firing drive assembly. The transitioning of the locking member 38 to the unlocked configuration causes the switch 208 to be transitioned to the inactive configuration 208a. In such instance, if the clinician attempts to actuate the firing trigger 16 from the unactuated position to the first actuated position, as described above, the switch 206 may be transitioned to the active configuration 206b but since the switch 208 is in the inactive configuration 208a, the indicator circuit 204 will not be closed and the indicator 205 will not be activated; and since the firing drive assembly is free from locking engagement with the locking member 38, the clinician may continue actuating the firing trigger 16 to advance the cutting member of the end effector 10 to cut the tissue captured between the jaws 22a, 22b, for example. In other words, the indicator 205 is not activated since the jaws 22a, 22b are sufficiently closed around captured tissue and, accordingly, the firing trigger 16 can be fully actuated in a complete firing stroke to advance the cutting member of the end effector 10 to cut the captured tissue.

Figure 5B:
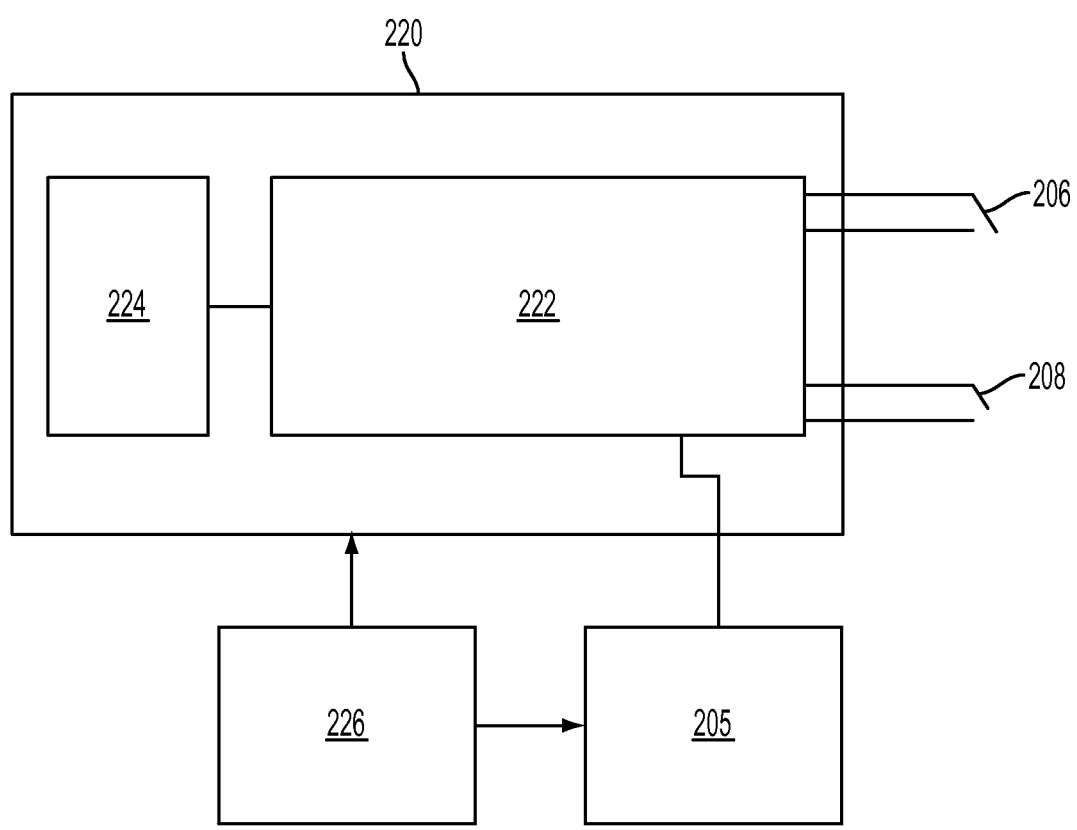
FIG. 5B illustrates a feedback system for use with the surgical instrument of FIG. 1.

In certain instances, as illustrated in FIG. 5B, the indicator 205, the switch 206, and the switch 208 can be operably coupled to a microcontroller 220 ("controller"), for example. In certain instances, the controller 220 may include a microprocessor 222 ("processor") and one or more memory units 224 operationally coupled to the processor 222, for example. A power source such as, for example, a battery 226 can be configured to supply power to the controller 220 and/or the indicator 205, for example. In certain instances, the memory 224 may include program instructions that can be executed from the memory 224 to cause the processor 220 to transmit activation signals to the indicator 205 in response to simultaneous active signals received from the switches 206 and 208, for example.

The controller 220 may be implemented using integrated and/or discrete hardware elements, software elements, and/or a combination of both. Examples of integrated hardware elements may include processors, microprocessors, microcontrollers, integrated circuits, application specific integrated circuits (ASIC), programmable logic devices (PLD), digital signal processors (DSP), field programmable gate arrays (FPGA), logic gates, registers, semiconductor devices, chips, microchips, chip sets, microcontrollers, system-on-chip (SoC), and/or system-in-package (SIP). Examples of discrete hardware elements may include circuits and/or circuit elements such as logic gates, field effect transistors, bipolar transistors, resistors, capacitors, inductors, and/or relays. In certain instances, the controller 220 may include a hybrid circuit comprising discrete and integrated circuit elements or components on one or more substrates, for example.

In certain instances, the microcontroller 220 may be an LM 4F230H5QR, available from Texas Instruments, for example. In certain instances, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, among other features that are readily available. Other microcontrollers may be readily substituted for use with the present disclosure. Accordingly, the present disclosure should not be limited in this context.

Figure 8:
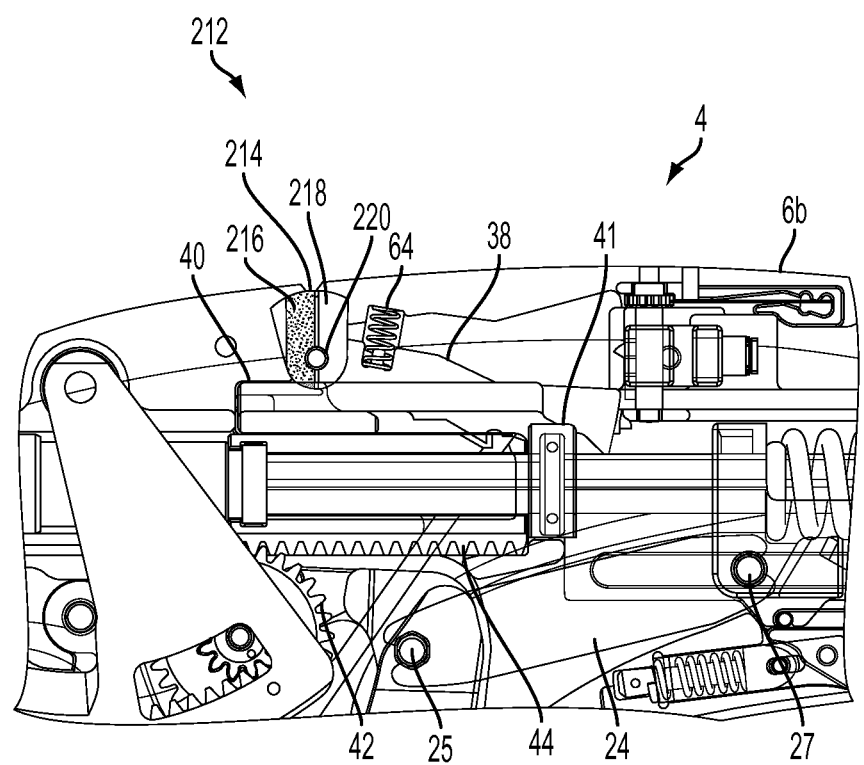
FIG. 8 illustrates a partial side view of a handle assembly of the surgical instrument of FIG. 1 with a removed housing shroud.
Figure 9:
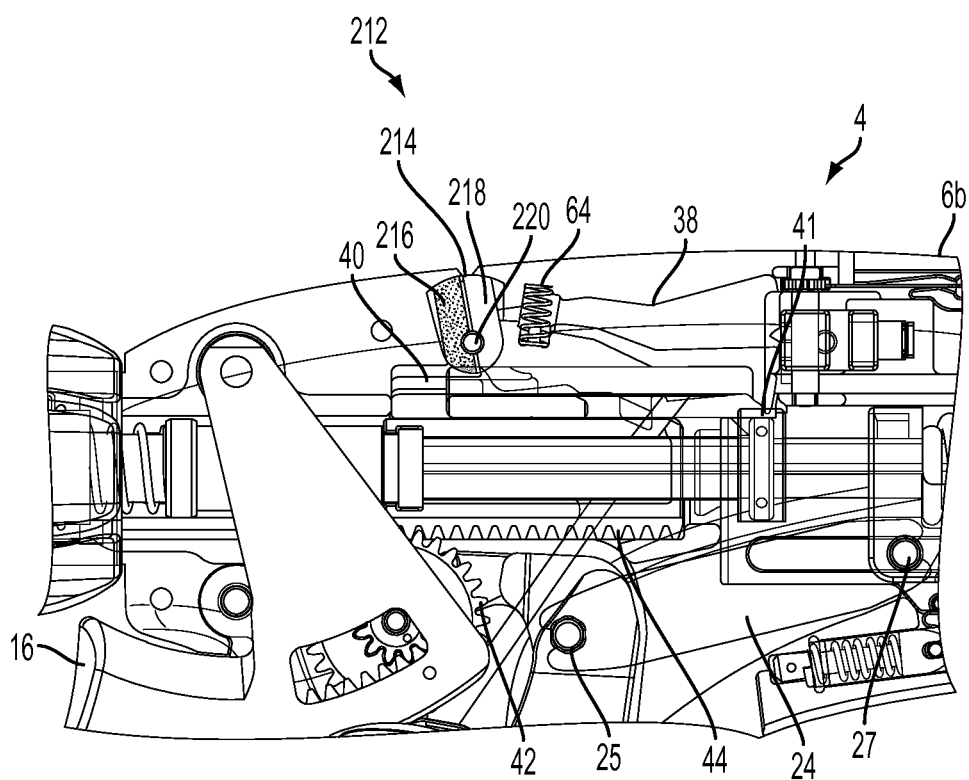
FIG. 9 illustrates a partial side view of a handle assembly of the surgical instrument of FIG. 1 with a removed housing shroud.

Referring to FIGS. 8 and 9, in certain instances, the surgical instrument 2 may comprise one or more mechanical feedback systems such as, for example, a mechanical feedback system 212. In certain instances, the mechanical feedback system 212 may replace the electrical feedback system 202, for example. In certain instances, the mechanical feedback system 212 can be employed to provide feedback to a clinician using the surgical instrument 2 as to the whether the firing drive assembly is locked, for example.

As illustrated in FIG. 8, the mechanical feedback system 212 may include an indicator window 214 positioned on an outer wall of the handle housing 4, for example. In addition, the mechanical feedback system 212 may include a locked indicator 216 which indicates that the firing drive assembly is locked, for example, and an unlocked indicator 218 which indicates that the firing drive assembly is unlocked, for example. In certain instances, as illustrated in FIG. 8, the indicators 216 and 218 can be operably coupled to the locking member 38. For example, as illustrated in FIG. 8, the indicators 216 and 218 can be pivotally coupled to the locking member 38 via a pivot member 220. In certain instances, the indicators 216 and 218 can be operably movable with the locking member 38 and can be aligned with the indicator window 214 such that the locked indicator 216 is visible from the indicator window 214, as illustrated FIG. 8, while the locking member 38 is in the locked configuration, and the unlocked indicator 218 is visible from the indicator window 214, as illustrated in FIG. 9, while the locking member 38 is in the unlocked configuration, for example.

In some instances, the jaws 22a, 22b are configured to maintain a minimal spacing therebetween to prevent damage to components of the surgical instrument 2 and/or the tissue section. In some instances, full actuation of the closure trigger 8 corresponds to a rotation of about 30 degrees. When the closure trigger 8 is fully rotated against the pistol grip handle 14, a closure trigger lock 46 is engaged to maintain the jaws 22a, 22b in a closed position. Once the trigger lock 46 has been engaged, the clinician may release the closure trigger 8 and the trigger lock 46 maintains the closure trigger 8 in a closed position.

In certain instances, the trigger lock 46 may maintain the closure trigger 8 in a less than fully retracted position to prevent damage to components of the surgical instrument 2 due to over application of force to the jaws 22a, 22b. The trigger lock 46 may maintain the closure trigger 8 in a sufficiently rotated position to release the locking member 38 from the rack unlock block 40. For example, in the some instances, the trigger lock 46 maintains the closure trigger 8 at a rotation of about 28 degrees. With the closure trigger 8 in a locked position, the clinician may actuate the firing trigger 16 to deploy the cutting member within the end effector 10. In some instances, the clinician may actuate the energy button 18 to deliver energy to a tissue section grasped between the jaws 22a, 22b prior to or simultaneously with, deployment of the cutting member.

Figure 10:
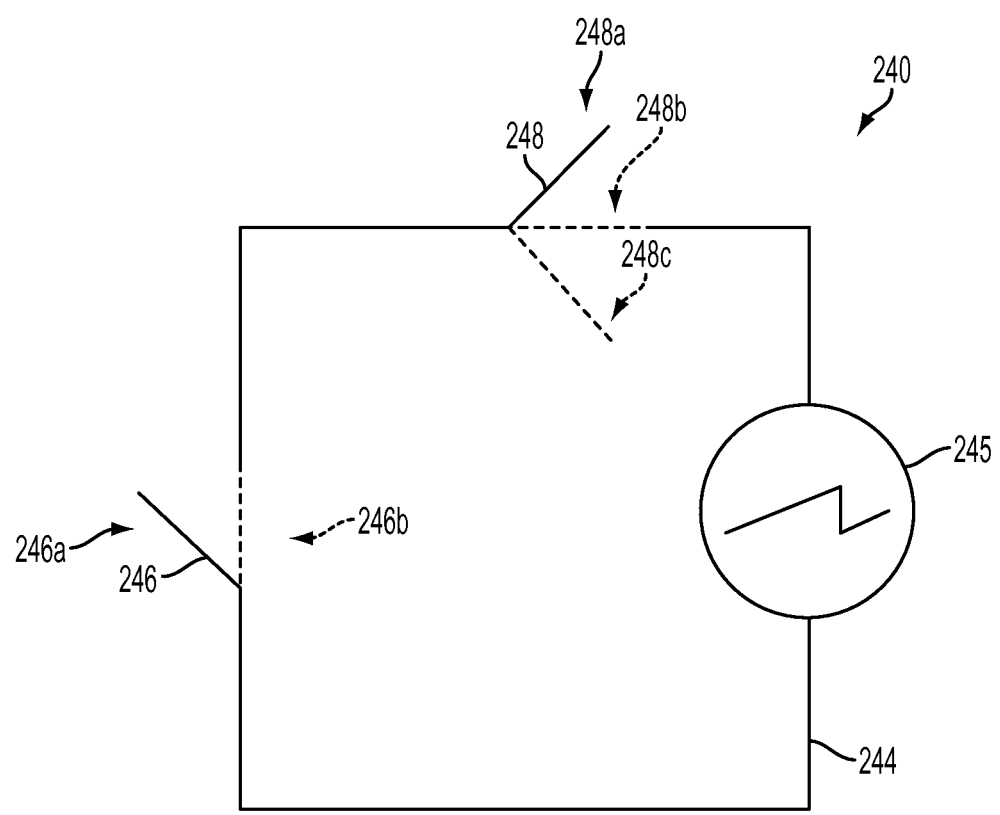
FIG. 10 illustrates a feedback system including an indicator circuit for use with the surgical instrument of FIG. 1.
Figure 11:
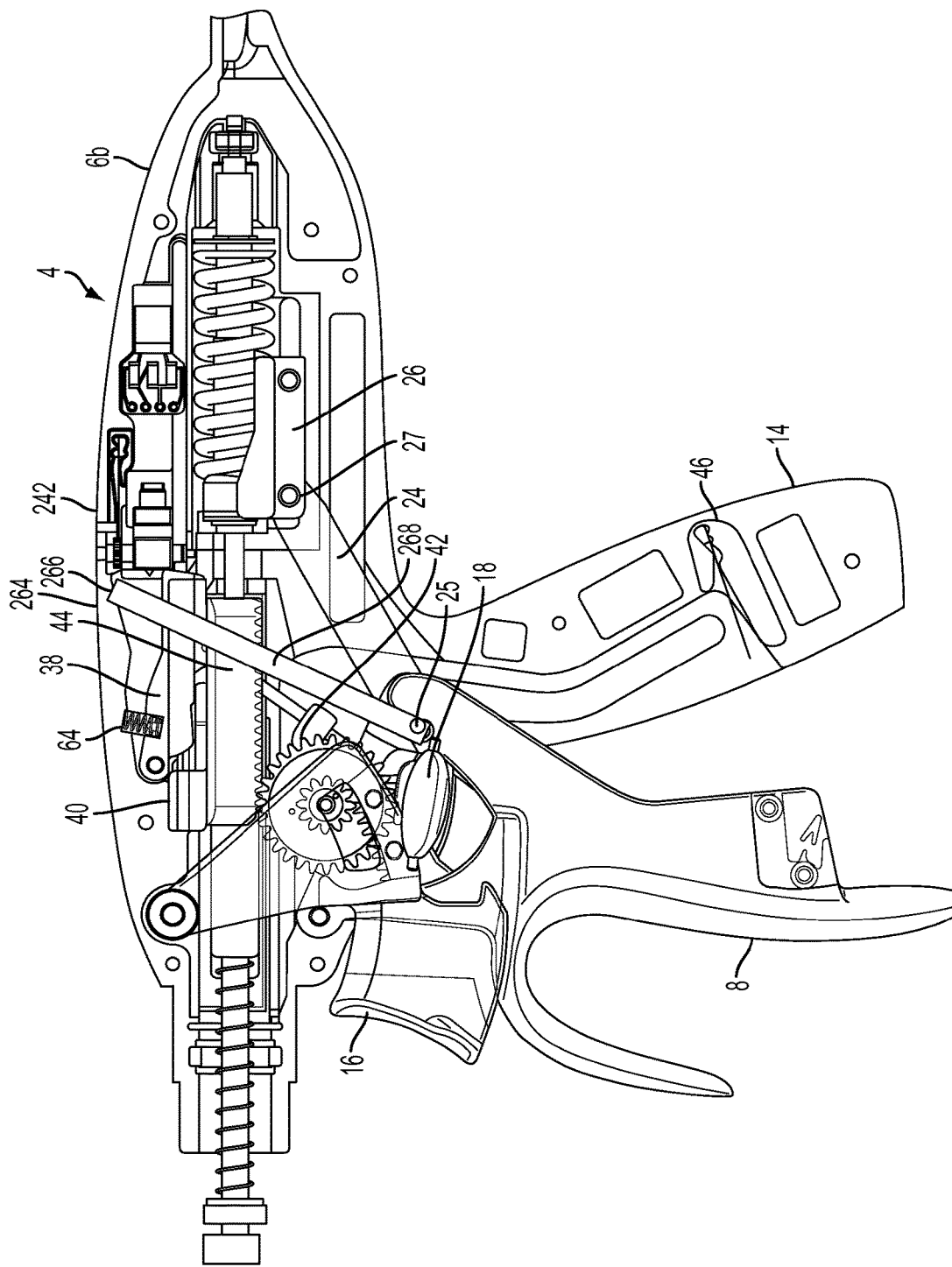
FIG. 11 illustrates a partial side view of a handle assembly of the surgical instrument of FIG. 1 with a removed housing shroud.

Referring to FIGS. 10 and 11, the surgical instrument 2 may include closure feedback systems that are associated with the closure trigger 8 such as, for example, an electrical feedback system 240 and/or a mechanical feedback system 242. As described above, the closure trigger 8 is actuatable between an initial unactuated position and an actuated locked position to close the jaws 22a, 22b around tissue, for example. In certain instances, the closure feedback systems 240 and/or 242 may be configured to warn or alert a clinician actuating the trigger 8 in the event the captured tissue comprises a thickness that cannot be properly treated utilizing the surgical instrument 2. In certain instances, the closure feedback systems 240 and/or 242 may be configured to warn or alert a clinician actuating the trigger 8 in the event the tissue captured between the jaws 22a, 22b cannot be safely compressed to a thickness that is less than or equal, or at least substantially equal, to the height of the cutting surface of the cutting member of the end effector 10, for example. In certain instances, the closure feedback systems 240 and/or 242 may be configured to warn or alert a clinician if the actuation force exerted against the trigger 8 by the clinician exceeds a safe threshold, for example. In certain instances, the closure feedback systems 240 and/or 242 may be configured to warn or alert a clinician actuating the trigger 8 in the event the tissue captured between the jaws 22a, 22b prevents approximation for the end effector 10 during a closure stroke from a first approximated configuration, for example, to a second approximated configuration, for example. In certain instances, the first approximated configuration corresponds to a tissue thickness that is not safely treatable by the surgical instrument 2; and the second approximated configuration corresponds to a tissue thickness that is safely treatable by the surgical instrument 2.

Referring to FIG. 10, the electrical feedback system 240 may include an indicator circuit 244. In certain instances, the indicator circuit 244 may comprise an indicator 245. In certain instances, the circuit 244 may include a plurality of switches such as, for example, normally open, normally closed, and/or other switch types. In certain instances, the circuit 244 may include a switch 246 which may be associated with the closure trigger 8, for example. In certain instances, the switch 246 can be transitioned between an inactive or open configuration or position 246a and an active or closed configuration or position 246b, as illustrated in FIG. 10. In certain instances, the switch 246 can be coupled to the closure trigger 8 such that actuation of the closure trigger 8 between the initial unactuated position and the actuated locked position during the closure stroke may cause the switch 246 to move from the inactive configuration 246a to the active configuration 246b, for example.

Further to the above, as illustrated in FIG. 10, the circuit 244 may comprise a switch 248. In certain instances, the switch 248 can be transitioned between a first inactive or open configuration or position 248a, an active or closed configuration or position 248b, and a second inactive or open configuration or position 248c during the closure stroke, for example. In certain instances, the switch 248 can be associated with one of the jaws 22a, 22b, for example. In certain instances, the switch 248 can be coupled to the jaw 22a, for example, such that motion of the jaw 22a during the closure stroke from an open unactuated or initial position to a first actuated position may cause the switch 248 to be transitioned from the first inactive configuration 248a, for example, to the active configuration 248b, for example; and motion of the jaw 22a during the closure stroke beyond the first actuated position to a second actuated position, for example, may cause the switch 248 to be transitioned from the active configuration 248b, for example, to the second inactive configuration 248c, for example. In certain instances, the circuit 244 can be closed and the indicator 245 can be activated when the switches 246 and 248 are in the closed configurations 246b and 248b, respectively.

In use, a clinician may position the jaws 22a, 22b around tissue and may actuate the closure trigger 8 through a closure stroke to actuate the jaws 22a, 22b to clamp the tissue, for example. In certain instances, the first actuated position of the jaw 22a can be associated with a first tissue thickness, for example; and the second actuated position of the jaw 22a can be associated with a second tissue thickness, for example. In certain instances, the first tissue thickness is too large for proper treatment with the surgical instrument 2. In certain instances, the second tissue thickness is suitable for treatment with the surgical instrument 2. In certain instances, if the tissue clamped between the jaws 22a, 22b comprises the first tissue thickness, the jaw 22a may remain in the first actuated position and may not be able to transition beyond the first actuated position to the second actuated position, as the clinician continues to actuate the trigger 8, due to the large thickness of the tissue clamped between the jaws 22a, 22b. Accordingly, the switch 248 may remain in the active configuration 248b, for example. If the clinician continues actuating the closure trigger 8 through the remainder of the actuation stroke, the closure trigger 8 may ultimately reach the actuated locked position; at such instance, the switch 246 may reach the active configuration 246b and since the switch 248 is also in the active configuration 248b, the circuit 244 will become closed and the indicator 245 activated to alert the clinician that the captured tissue comprises a thickness that is too large for proper treatment with the surgical instrument 2.

The reader will appreciate that if the tissue clamped between the jaws 22a, 22b comprises a thickness suitable for treatment via the instrument 2 such as, for example, the second tissue thickness, the jaw 22a may continue to move past the first actuated position and toward the second actuated position as the clinician continues to actuate the trigger 8 through the closure stroke. Accordingly, the switch 248 may move past the active configuration 248b to the inactive configuration 248c. If the clinician continues actuating the closure trigger 8 through the remainder of the actuation stroke, the closure trigger 8 may ultimately reach the actuated locked position; at such instance, the switch 246 may reach the active configuration 246b. But since the switch 248 is in the inactive configuration 248c, the circuit 244 will remain open and the indicator 245 will remain inactive when the switch 246 reaches the closed configuration 246b. In other words, since the tissue clamped between the jaws 22a, 22b comprises a thickness that is not too large for treatment with the surgical instrument 2, the indicator 245 may remain inactive.

In certain instances, the switch 248 can be associated with the closure drive assembly at a position proximal to the jaw 22a and can be operable in a similar manner as described above. In certain instances, the switch 248 can be associated with the jaw 22b and can be operable in a similar manner as described above. In certain instances, the circuit 244 may comprise a third switch (not shown) which can be associated with the jaw 22b such that the circuit 244 is closed and the indicator 245 is activated when the third switch and the switches 246 and 248 are all in the active configuration, for example.

Figure 12:
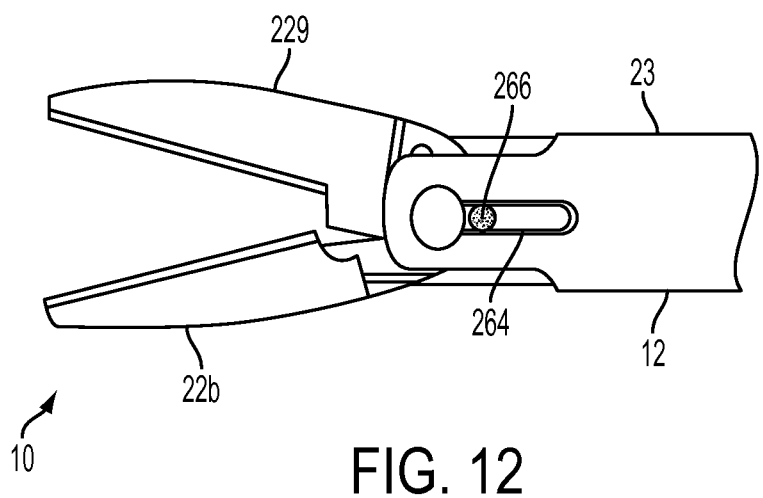
FIG. 12 illustrates a side view of an end effector assembly and a partial shaft assembly of the surgical instrument of FIG. 1 including an indicator visible through an indicator window.

Referring to FIG. 11, in certain instances, the mechanical feedback system 242 may replace the electrical feedback system 240, for example, to provide feedback to a clinician actuating the trigger 8 in the event the tissue clamped between the jaws 22a, 22b comprises a thickness that cannot be properly treated with the surgical instrument 2. As illustrated in FIG. 11, the mechanical feedback system 242 may include an indicator window 264 positioned on an outer wall of the handle housing 4, for example. In certain instances, as illustrated in FIG. 12, the indicator window 264 can be positioned on the outer sheath 23 of the shaft assembly 12, for example.

Figure 14:
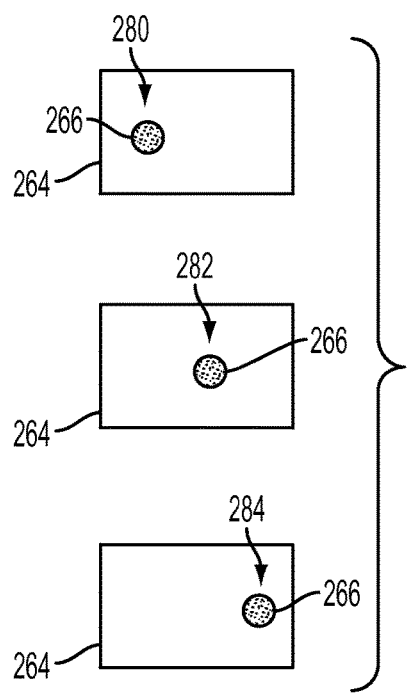
FIG. 14 illustrates an indicator of a feedback system of the surgical instrument of FIG. 1 in a plurality of indicator positions relative to an indicator window.
Figure 15:
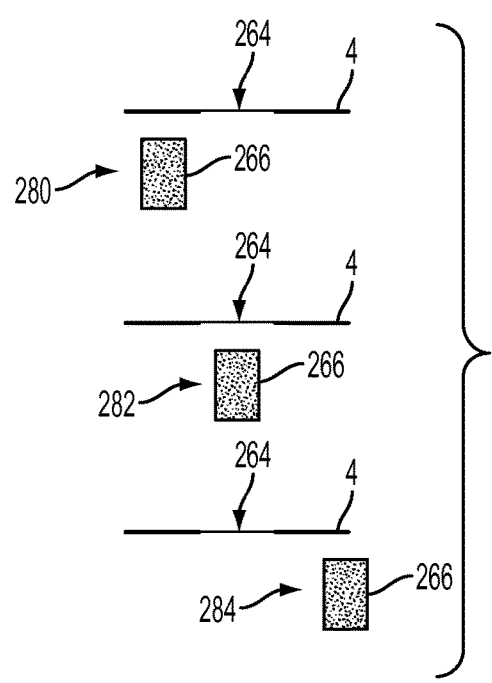
FIG. 15 illustrates an indicator of a feedback system of the surgical instrument of FIG. 1 in a plurality of indicator positions relative to an indicator window.

In any event, the mechanical feedback system 242 may include an indicator 266. In certain instances, as illustrated in FIGS. 14 and 15, the indicator 266 can be movable between a first indicator position 280, a second indicator position 282, and a third indicator position 284, for example. In certain instances, as illustrated in FIG. 15, the indicator 266 is not visible through the indicator window 264 while in the first indicator position 280 and while in the third indicator position 284. However, in certain instances, the indicator 266 is visible through the indicator window 264 while in the second indicator position 282, for example. In certain instances, the indicator 266 is movable between a plurality of indicator positions that may be defined by color coded sections depicted on the outer sheath 23, for example.

In certain instances, as illustrated in FIG. 11, the indicator 266 can be movably coupled to the closure drive assembly via an indicator arm 268, for example. In certain instances, the indicator 266 can be pivotally coupled to the closure drive assembly of the surgical instrument 2 such that motion of the closure drive assembly between a first closure position corresponding to the unactuated open position of the jaw 22a, a second closure position corresponding to the first actuated position of the jaw 22a, and a third closure position corresponding to the second actuated position of the jaw 22a may cause the indicator 266 to move between the first indicator position, the second indicator position, and the third indicator position, respectively, for example.

In use, a clinician may position the jaws 22a, 22b around tissue and may actuate the closure trigger 8 through a closure stroke to actuate the jaws 22a, 22b to clamp the tissue, for example. As the clinician actuates the trigger 8, the closure drive assembly may be transitioned from the first closure position to the second closure position which may cause the jaw 22a to be transitioned from the initial unactuated position to the first actuated position, and may cause the indicator 266 to be transitioned from the first indicator position 280 to the second indicator position 282. As described above, the indicator 266 may be visible through the indicator window 264 in the second indicator position 282. Also described above, if the tissue clamped between the jaws 22a, 22b comprises the first tissue thickness, the jaw 22a may remain in the first actuated position and may not be able to transition to the second actuated position, as the clinician continues to actuate the trigger 8, due to the large thickness of the tissue clamped between the jaws 22a, 22b. Accordingly, the indicator 266 may remain in the second indicator position 282 and may remain visible through the indicator window 264 to provide the clinician with feedback that the captured tissue cannot be properly treated with surgical instrument 2, for example.

The reader will appreciate that if the tissue clamped between the jaws 22a, 22b comprises a thickness suitable for treatment with the instrument 2 such as, for example, the second tissue thickness, the closure drive assembly may continue to move past the second closure position to the third closure position, for example, and the jaw 22a may continue to move past the first actuated position to the second actuated position, for example, as the clinician continues to actuate the trigger 8 through the closure stroke. In result, the indicator 266 may be moved past the second indicator position 282 toward the third indicator position 284, for example, and away from indicator window 264.

Figure 13:
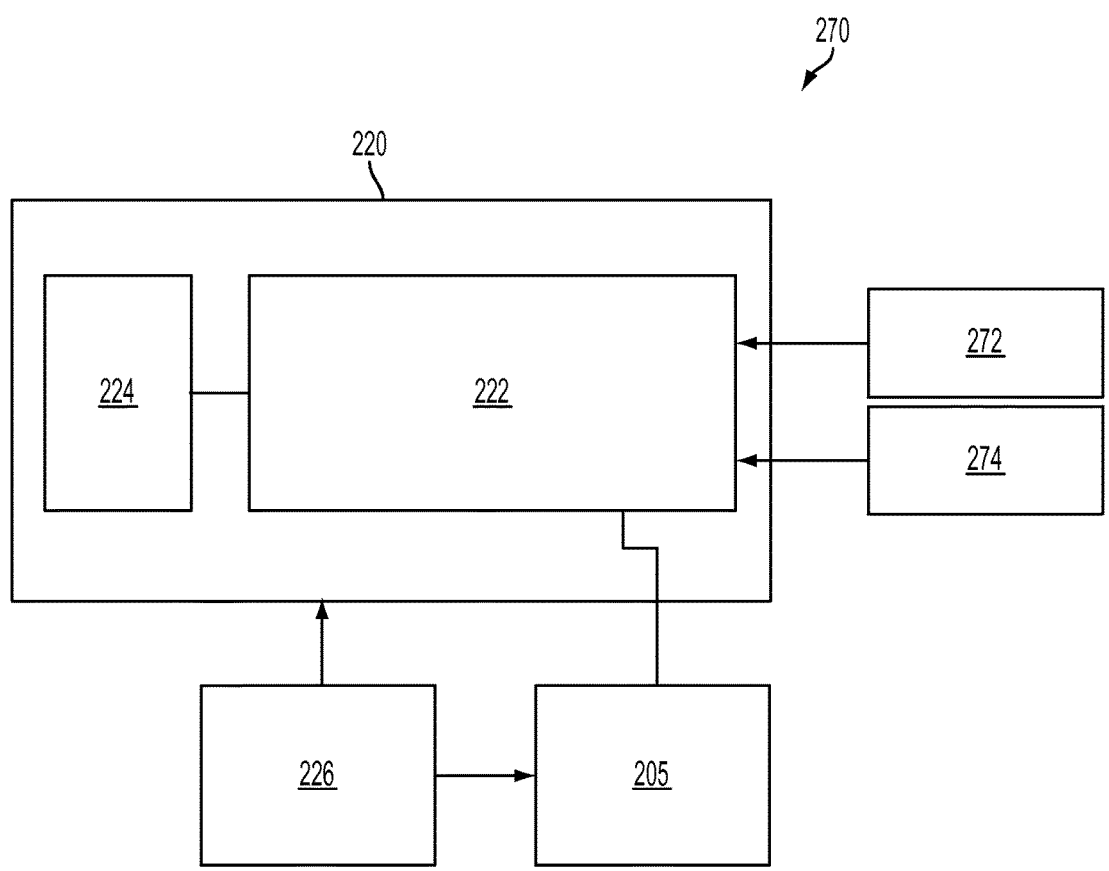
FIG. 13 illustrates a feedback system for use with the surgical instrument of FIG. 1.

In certain instances, referring to FIG. 13, the surgical instrument 2 may include one or more feedback systems such as, for example, a feedback system 270. In certain instances, as illustrated in FIG. 13, the feedback system 270 may include the controller 220 which may include the processor 222 and the memory 224, for example. In certain instances, the feedback system 270 can be powered by a power source such as, for example, the battery 226. In certain instances, the feedback system 270 may comprise one or more indicators such as, for example, the indicator 205. In certain instances, the feedback system 270 may comprise one or more load cells such as, for example, strain gauges 272 and 274.

Strain gauges suitable for use in the present invention include (a) feedback electroactive polymer elements whose impedance or resistance varies as a function of the amount of strain in the device and (b) conventional strain gauges in which the resistance of the device varies as a function of the amount of strain in the device, thus allowing the amount of strain to be readily quantified and monitored. Such strain gauges are commercially from a number of different sources, including National Instruments Co., Austin, Tex., and include piezoresistive strain gauges (for which resistance varies nonlinearly with strain) and bonded metallic strain gauges (for which resistance typically varies linearly with strain). The later strain gauges consist of very fine wire or metallic foil that is arranged in a grid pattern. The grid is bonded to a thin backing or carrier, which may be directly attached to the substrate being monitored for strain. Consequently, the strain experienced by the substrate is transferred directly to the strain gauge, which responds with a change in electrical resistance. Commercially available strain gauges typically have nominal resistance values within the range of 30 to 3000Ω, with 120Ω, 350Ω and 1000Ω devices being especially common.

In certain instances, the strain gauge 272 is operable to monitor closure actuation forces applied by a clinician to the surgical instrument 2 through the closure trigger 8, for example. In certain instances, the strain gauge 272 can be placed on various locations of the surgical instrument 2 that are associated with the closure stroke. In certain instances, the strain gauge 272 can be placed on the closure drive, for example. In certain instances, the strain gauge 272 can be placed on the closure trigger 8, for example. In certain instances, the strain gauge 272 can be placed on toggle arm 24, for example.

In certain instances, the strain gauge 274 is operable to monitor firing actuation forces applied by a clinician to the surgical instrument 2 through the firing trigger 16, for example. In certain instances, the strain gauge 274 can be placed on various locations of the surgical instrument 2 that are associated with the firing stroke. In certain instances, the strain gauge 274 can be placed on the firing drive, for example. In certain instances, the strain gauge 274 can be placed on the firing trigger 16, for example.

In certain instances, the memory 224 may include program instructions that can be executed from the memory 224 to cause the processor 220 to monitor strain measurements transmitted from the strain gauge 272 and/or the strain gauge 274 to the processor 222. In certain instances, the strain measurements of the strain gauge 272 and/or the strain gauge 274 can be transmitted to the processor 222 through an analogue to digital converter, for example. In certain instances, the memory 224 may include program instructions that can be executed from the memory 224 to cause the processor 220 to detect an increase in the monitored closure actuation forces beyond a predetermined threshold and to transmit an activation signal to the indicator 205 in response to the detection of such an increase. In certain instances, the memory 224 may include program instructions that can be executed from the memory 224 to cause the processor 220 to detect an increase in the monitored firing actuation forces beyond a predetermined threshold and to transmit an activation signal to the indicator 205 in response to the detection of such increase.

The reader will appreciate one or more of the switches described by the present disclosure may comprise mechanical switches, electro-mechanical switches, and/or solid state switches. In certain instances, one or more of the switches of the present disclosure may comprise open, inactive, and/or non-conductive positions, states, and/or configurations. In certain instances, one or more of the switches of the present disclosure may comprise closed, active, and/or conductive positions, states and/or configurations. In certain instances, one or more of the switches of the present disclosure can be transitioned from the open, inactive, and/or non-conductive positions, states, and/or configurations to the closed, active, and/or conductive positions, states and/or configurations to close and/or activate one or more circuits associated with such switches, for example.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A surgical instrument, comprising:
    a shaft;
    an end effector extending distally from the shaft, the end effector comprising:
        a first jaw;
        a second jaw, wherein at least one of the first jaw and the second jaw is movable relative to the other one of the first jaw and the second jaw to transition the end effector between an open configuration and an approximated configuration;
        an electrode operable to seal tissue captured between the first jaw and the second jaw in the approximated configuration; and
        a cutting member movable to cut the tissue captured between the first jaw and the second jaw in the approximated configuration;
    a housing extending proximally from the shaft, the housing comprising:
        a closure trigger actuatable in a closure stroke to transition the end effector from the open configuration to the approximated configuration, the closure trigger movable between an initial unactuated position and an actuated position during the closure stroke; and
        a firing trigger actuatable in a firing stroke to advance the cutting member to cut the tissue captured between the first jaw and the second jaw in the approximated configuration; and
    a feedback system comprising an indicator circuit, the indicator circuit comprising:
        a first switch transitionable between a first switch inactive configuration and a first switch active configuration, the first switch associated with the closure trigger, wherein the actuation of the closure trigger from the initial unactuated position to the actuated position transitions the first switch from the first switch active configuration to the first switch inactive configuration;
        a second switch transitionable between a second switch inactive configuration and a second switch active configuration, the second switch associated with the firing trigger, wherein actuation of the firing trigger transitions the second switch from the second switch inactive configuration to the second switch active configuration; and
        an indicator activated when the first switch is in the first switch active configuration and when the second switch is in the second switch active configuration.

2. The surgical instrument of claim 1, further comprising a locking member movable between a locked position and an unlocked position.

3. The surgical instrument of claim 2, wherein the locking member, in the locked position, is configured to resist advancement of the cutting member to cut the tissue captured between the first jaw and the second jaw in the approximated configuration.

4. The surgical instrument of claim 3, wherein the first switch is in the first switch active configuration when the locking member is in the locked position.

5. The surgical instrument of claim 4, wherein the first switch is in the first switch inactive configuration when the locking member is in the unlocked position.

6. The surgical instrument of claim 1, wherein the firing trigger is actuatable during the firing stroke to a first actuated position and to a second actuated position beyond the first actuated position.

7. The surgical instrument of claim 6, wherein the second switch is in the second switch active configuration when the firing trigger is in the first actuated position.

8. The surgical instrument of claim 7, wherein the cutting member comprises a cutting surface, and wherein the cutting surface is configured to contact the tissue when the firing trigger is in the second actuated position.

9. A surgical instrument, comprising:
    an end effector, the end effector transitionable between an open configuration, a first approximated configuration, and a second approximated configuration;
    a closure drive assembly movable in a closure stroke to transition the end effector from the open configuration to the first approximated configuration and further to the second approximated configuration;
    a cutting member;
    a firing drive assembly;
    a firing trigger operably coupled to the firing drive assembly, the firing trigger actuatable in a firing stroke between an initial unactuated position, a first actuated position, and a second actuated position, wherein the firing trigger is movable from the first actuated position to the second actuated position to motivate the firing drive assembly to advance the cutting member to engage tissue captured by the end effector in the second approximated configuration; and
    a feedback system comprising an indicator circuit, the indicator circuit comprising:
        a first switch transitionable between a first switch open position and a first switch closed position, wherein the first switch is in the first switch closed position when the end effector is in the first approximated configuration, and wherein the first switch is in the first switch open position when the end effector is in the second approximated configuration;

a second switch transitionable between a second switch open position and a second switch closed position, wherein the second switch is in the second switch open position when the firing trigger is in the initial unactuated position, and wherein the second switch is in the second switch closed position when the firing trigger is in the first actuated position; and an indicator activated when the first switch is in the first switch closed position and when the second switch is in the second switch closed position.

10. The surgical instrument of claim 9, further comprising a locking member movable between a locked position and an unlocked position.

11. The surgical instrument of claim 10, wherein the locking member is in the locked position when the end effector is in the first approximated configuration.

12. The surgical instrument of claim 11, wherein the locking member is in the unlocked position when the end effector is in the second approximated configuration.

13. The surgical instrument of claim 12, wherein the locking member is configured to engage the firing drive assembly in the locked position.

14. The surgical instrument of claim 13, wherein the locking member is configured to release the firing drive assembly in the unlocked position.

15. The surgical instrument of claim 14, wherein the first switch is coupled to the locking member, wherein movement of the locking member from the locked position to the unlocked position transitions the first switch from the first switch closed position to the first switch open position.

16. A surgical instrument, comprising:
a shaft;
a handle extending proximally from the shaft, the handle comprising a closure trigger actuatable in a closure stroke between an initial unactuated position and a locked actuated position;
an end effector extending distally from the shaft, the end effector operably coupled to the closure trigger, wherein the end effector comprises:
a first jaw; and
a second jaw, wherein at least one of the first jaw and the second jaw is movable relative to the other one of the first jaw and the second jaw to transition the end effector during the closure stroke between an open configuration, a first approximated configuration, and a second approximated configuration; and
a feedback system including an indicator circuit, the indicator circuit comprising:
a first switch transitionable between a first open position, an intermediate closed position, and a second open position, wherein the first switch is in the first open position when the end effector is in the open configuration, wherein the first switch is in the intermediate closed position when the end effector is in the first approximated configuration, and wherein the first switch is in the second open position when the end effect is in the second approximated configuration;
a second switch transitionable between an open position and a closed position, wherein the second switch is in the open position when the closure trigger is in the initial unactuated position, and wherein the second switch is in the closed position when the closure trigger is in the locked actuated position; and
an indicator, the indicator activated when the first switch is in the intermediate closed position and when the second switch is in the closed position.

17. The surgical instrument of claim 16, wherein the first switch is movably coupled to the first jaw.

* * * * *